(12) United States Patent
Mitchell

(10) Patent No.: US 6,630,455 B1
(45) Date of Patent: Oct. 7, 2003

(54) METHODS FOR INDUCING MUCOSAL IMMUNE RESPONSES

(75) Inventor: William M. Mitchell, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 08/372,429

(22) Filed: Jan. 13, 1995

(51) Int. Cl.$^7$ .................. A01N 43/04; A61K 31/70; C12N 15/00; C12N 15/88

(52) U.S. Cl. .................. 514/44; 435/440; 435/458

(58) Field of Search ...................... 435/69.1, 172.3, 435/320.1, 172.1, 240.1, 440, 458; 424/200.1, 130.1, 184.1; 514/44, 2, 731

(56) References Cited

U.S. PATENT DOCUMENTS

| | | | |
|---|---|---|---|
| 5,171,678 A | 12/1992 | Behr et al. | 435/172.3 |
| 5,294,441 A * | 3/1994 | Curtiss, III | 424/200.1 |
| 5,328,470 A | 7/1994 | Nabel et al. | 604/101 |
| 5,459,127 A | 10/1995 | Felgner et al. | 514/7 |
| 5,908,635 A | 6/1999 | Thierry | 424/450 |
| 6,348,449 B1 * | 2/2002 | Weiner et al. | 514/44 |

FOREIGN PATENT DOCUMENTS

| | | |
|---|---|---|
| WO | WO 93/19768 | 10/1993 |
| WO | WO 94 27435 A | 12/1994 |
| WO | WO 96 40964 A | 12/1996 |

OTHER PUBLICATIONS

Makela et al., Vaccine 14: 719–731 1996, "Aminal Models For Vaccines to Prevent Infectious Diseases".*
Wang et al., PNAS, USA, 90:4156–4160, 1993.*
"NIH Report and Recommendation" Dec. 7, 1995, 1–40.*
Marshall, Science, 269, pp. 1050–1055, 1995.*
Gutierrez et al, Lancet, 339, pp. 715–721, 1992.*
Friedmann, Cancer, vol. 70, No. 6, pp. 1810–1817, 1992.*
Holmgren et al, Immunobiol., vol. 184, pp 157–179, 1992.*
Barthel et al, DNA and Cell Biology, Vol : 12(6) pp. 1993.*
Lehner et al, Proc. Natl. Acad. Sci., USA, vol. 90, pp. 8638–8642, 1992.*
Fynan et al, Proc. Natl. Acad. Sci., USA, vol. 90, pp. 11478–11482, 1993.*
McGhee et al, Reprod. Fertil. Dev., 1994, vol. 6, 369–379.*
Barthel et al. "Gene Transfer Optimization with Lipospermine–Coated DNA" *DNA and Cell Biol.* 12(6):553–560, 1993.
Barthel et al., "Gene Regulation Analysis by Lipopolyamine–Mediated DNA Transfer in Primary Neurons," Methods in Neurosciences 9:291–312 (1992).
Demeneix et al., "Gene transfer into intact vertebrate embryos," Int. J. Dev. Biol. 35:481–484 (1991).
Leventis et al., "Interactions of mammalian cells with lipid dispersions containing novel metabolizable cationic amphiphiles," *Biochimica et Biophysica Acta* 1023:124–132 (1990).
Wolff et al., "Direct Gene Transfer into Mouse Muscle in Vivo," *Science* 247:1465–1468 (1990).
Symons M. "Commentary Polyamines to Target Drugs to DNA" *Free Rad. Res.* 2291):1–9, 1995.
Remy et al. "Gene Transfer with a Series of Lipophilic DNA–Binding Moelcules" *Bioconjugate Chem.* 5:647–654, 1994.
Demeneix et al. "Temporal and Spatial Expression of Lipospermine–Compacted Genes Transferred . . . " *BioTechniques* 16(3):496–501, 1994.
Mack et al. "Cationic Lipid Enhances In Vitro Receptor= Mediated Transfection" *Am. J. Med. Sci.* 307(2):138–143, Feb. 1994.
Tung et al. "Polyamine–linked oligonucleotides for DNA Triple Helix Formation" *Nuc. Acids Res.* 21(23):5489–5494, 1993.
Mitchell et al. "An animal model for antibody–dependent enhancement of HIV infection:antibodies to the putative SIV . . . " *AIDS* 9(1), 8 pages, 1995, in press.
Koff, Wayne C. "Policy Forum:The next Steps Toward a Global AIDS Vaccine" *Science* 26:1335–1337, Nov. 25, 1994.
Robert F. Service "Research News:Triggering the first line of defense" *Science* 265:1522–1524, Sep. 9, 1994.
Jon Cohen "AIDS Vaccine Research:U.S. Panel Votes to Delay Real–World Vaccine Trials" *Science* 264:1839, Jun. 1994.

(List continued on next page.)

Primary Examiner—Deborah Crouch
Assistant Examiner—Thaian N. Ton
(74) Attorney, Agent, or Firm—Clark & Elbing LLP

(57) ABSTRACT

The invention provides a method of inducing a mucosal immune response in a subject, comprising administering to the mucosa of the subject an amount of antigen-encoding DNA effective to induce a mucosal immune response complexed to a transfection-facilitating lipospermine or a lipospermidine. In the method of inducing a mucosal immune response, the antigen-encoding DNA can encode an antigen that is expressed on the surface of infected cells during the course of infection. DNA encoding the envelope glycoproteins of viral pathogens is used in the present method. Lipospermines and lipospermidines are bifunctional molecules consisting of one or more hydrophobic chains covalently linked to a cationic grouping in which there is coordination of three or more amide hydrogens with a phosphate oxygen of the DNA chain forming an ionic charge complex. One preferred example of a lipospermine is DOGS (droctadecylamidoglycylspermine). The invention also provides a composition, comprising an amount of DNA encoding an envelope antigen or envelope-associated antigen of a pathogen complexed to a lipospermine. More specifically, the invention provides a composition, comprising an amount of DNA encoding an envelope antigen of HIV complexed to a lipospermine

7 Claims, 2 Drawing Sheets

OTHER PUBLICATIONS

Jon Cohen "AIDS Vaccines:Will Media Reports KO Upcoming Real–Life Trials?" *Science* 264:1660, Jun. 17, 1994.

Jon Cohen "News & Comment:The HIV Vaccine Paradox" *Science* 264:1072–1074 May 20, 1994.

Daynes et al. "The Development of Effective Vaccine Adjuvants Employing Natural Regulators . . . "*Ann. N.Y. Acad. of Sci.* 730:144–161, 1994.

Hui et al. "Generation of allo–reactive cytotoxic T lymphocytes by particle bombardment–mediated gene transfer" *J. Immunol. Metho.* 171:147–155, 1994.

Jon Cohen "News & Comment:Jitters Jeopardize AIDS Vaccine Trials" *Science* 262:980–981, Nov. 12, 1993.

Jon Cohen "Research News:Naked DNA Points Way to Vaccines" *Science* 259:1691–1692, Mar. 19, 1993.

Ulmer et al. "Heterologous Protection Against Influenza . . . " *Science* 259:1745–1748, Mar. 1993.

Gabriel et al. "Proposed atomic structure of a truncated human immunodeficiency virus glycoprotein gp120 . . . " *Proc. Natl. Sci. USA* 90:4186–4190, May 1993.

Editorial, *DNA and Cell Biol.* vol. 12, No. 9, pp. v, 1993.

Davis et al. "Direct Gene Transfer into Skeletal Muscle in vivo . . . " *Human Gene Therapy,* Mary Ann Liebert, Inc., Pub., 4:151–159, 1993.

Wang et al. "DNA Inoculation induces Neutralizing Immune Responses Against Human Immunodeficiency . . . " *DNA and Cell Biol.* 12(9):799–805, 1993.

Yankauckas et al. "Long–Term Anti–Nucleoprotein Cellular and Humoral Immunity is Induced . . . " *DNA and Cell Biol.* 12(9):771–776, 1993.

Wang et al. "Gene inoculation generates immune responses against human . . . " *Proc. Natl. Sci. USA* 90:4156–4160, May 1993.

Davis et al. "DNA–based immunization induces continuous secretion of hepatitis B surface antigen . . . " *Human Mol. Genetics* 2(11):1847–1851, 1993.

Fynan et al. "Use of DNA Encoding Influenza Hemagglutinin as an Avian . . . " *DNA and Cell Biol.* 12(9):785–789, 1993.

Eisenbraun et al. "Examination of Parameters Affecting the Elicitation of Humoral Immune Responses . . . " *DNA and Cell Biol.* 12(9):791–797, 1993.

Davis et al. "Plasmid DNA is superior to viral vectors for direct gene transfer into adult . . . " *Human Gene Therapy,* Mary Ann Liebert, 4:733–740, 1993.

Montgomery et al. "Heterologous and homologous protection against influenza A by . . . " *DNA and Cell Biol.* 12(9):777–783, 1993.

Barthel et al. "Laboratory methods—Gene Transfer Optimization with Lipospermine–coated DNA" *DNA and Cell Biol.* 12(6):553–560, 1993.

Tang et al. :Genetic immunization is a simple method for eliciting an immune response *Nature* 356:152–154, Mar. 1992.

Behr et al. "Efficient gene transfer into mammalian primary endocrine cells with lipopolyamine–coated DNA" *Proc. Natl. Sci. USA* 86:6982–6986, Sep. 1989.

* cited by examiner

METHODS FOR INDUCING MUCOSAL IMMUNE RESPONSES

This invention was made with government support under rant numbers R01 AI 31371, NIH-AI33815 and 1 R01 AI36488-01. The government has certain rights in the invention.

BACKGROUND OF THE INVENTION

1. Field of the Invention

The present invention is directed to mucosal immunity. Specifically, the invention is directed to a method of inducing mucosal immunity in a subject. More specifically, the invention is directed to a method of inducing mucosal immunity in a subject by administering DNA complexed to a lipospermine to the mucosa of the subject.

2. Background Art

Mucosal surfaces represent the major route of entry for most systemic pathogens with subsequent mucosal immunity usually providing long-term protection against reinfection (25). Examples include,the life-long immunity produced by the Sabin oral polio vaccine versus the relatively short-term protection provided by,the Salk parenteral vaccine (48) and the single dose oral cholera vaccine with its improved safety profile versus the older multi-dose parenteral cholera vaccine (27). The best long-term mucosal and systemic protection against infection is provided by live, attenuated pathogens which simulate infection of the naive host but which are incapable of inducing disease (28). Despite the current capacity to produce attenuating mutations in cloned microorganisms, the concern over potential reversion to virulence or host virulence determinants has effectively inhibited development of live attenuated pathogens as. inducers of mucosal immunity for human use (29).

For example, at the most recent meeting of the NIH sponsored HIV vaccine meeting in November 1994, the proponents of attenuated live virus vaccines received a blow by Ruth Ruprecht (29) who reported that an attenuated SIV (i.e., Nef deletion)was responsible for the development of AIDS in newborn Rhesus macaques who had received the vaccine. It is unlikely that an attenuated HIV will ever receive FDA approval as an HIV vaccine.

The World Health Organization (WHO) estimates that by the year 2000 at least 40 million people, will be infected with the Human Immunodeficiency Virus (HIV). Due to the relentless and progressive pathogenesis of the virus the majority of those infected will-die within 10 years. It is estimated further that the death toll will be at 10 million as we enter the 21st century. Despite an initial massive effort by industry to develop a vaccine, few commercial developers remain. NIH's National HIV Vaccine recently received a critical blow when the AIDS Research Advisory Program Committee (ARAC) voted to not proceed in Phase III clinical testing of the two leading candidate subunit vaccines.

Another difficulty with the current efforts to develop an HIV vaccine is the paucity of research in the generation of mucosal immune responses to HIV. Epidemiological data clearly indicate that 70–80% of all AIDS cases are the result of heterosexual transmission of HIV (30–38). Heterosexual transmission is the fastest. growing route of transmission in the United States with women being at significantly greater risk of infection by HIV than males (39,40). Since 90% of HIV is transmitted sexually worldwide, it is unlikely that systemic-immunity will block initial infection at the mucosal sites of entry. Infection of Langerhans cells, mucosal macrophages, T cells, and even epithelial cells from cell associated HIV or free HIV in semen of the genital tract is a powerful argument that the induction of mucosal responses are at least as important as systemic responses in the development of a vaccine against HIV infection (35–37, 41). Although systemic immunization rarely induces mucosal immunity, mucosal immunization frequently provides systemic responses as well (36,41,42,43,44,45,46). It is essential that more effort be devoted to this key element in establishing a primary defense against, HIV transmission. With the clear danger of using live attenuated virus, the prospects for inducing mucosal immunity are difficulty.

Recent developments in vaccine research include the demonstration that transfection of mouse muscle with a bacterial plasmid carrying the DNA sequence encoding an influenza virus nucleoprotein resulted in the development of humoral and cellular responses which protected mice from lethal viral challenge (1). Two methods of transfection in vivo have been reported previously to achieve genetic immunization. The more common approach follows the observation that mouse muscle is a unique, target for transfection with naked DNA (3) and that muscle of a variety of species is particularly susceptible to naked DNA transfection (4–11). Protection against lethal challenge in mice by influenza A virus, and induction of cytotoxic lymphocytes and neutralizing antibodies to influenza A virus (1,13–15) and HIV (16,17), following genetic IM immunization has been reported by a number of investigators. Despite the impressive induction of protective immune responses, this method has the disadvantage that relatively massive quantities of DNA are required. Although unreported as a toxic side effect to date, this requirement for large quantities of DNA may limit this method due to the potential for antibody response to DNA itself and the generation of a self-sustaining lupus-like syndrome. The less common approach to genetic immunization using bolistic transformation overcomes the problem of DNA quantity but requires instrumentation not widely available. Typically, nanogram quantities of DNA complexed to gold or tungsten particles are physically propelled through the plasma membrane by microprojectile bombardment. Both methods elicit cellular (21,22) and humoral responses (22–24). However, neither of the above methods of genetic immunization induce mucosal immunity.

Despite the importance of mucosal immunity for an effective immunization strategy, the only FDA approved vaccine that induces mucosal immunity is the Sabin, live-attenuated oral polio vaccine. More recently, another development in the generation of mucosal immunity was the demonstration that the systemic administration of activated vitamin D3 (1,25-dihydroxycalciferol [$1,25(OH)_2D3$]) with conventional protein antigens converts a systemic response to a mucosal response (2). Thus, the art is actively seeking ways to induce a mucosal immune response.

The present invention meets a very important need in vaccine production by providing a method to induce in vivo mucosal immune responses to antigens of pathogens by the facilitated transfection of mucosa with a bacterial plasmid carrying the DNA sequence for the antigen.

SUMMARY OF THE INVENTION

The invention provides a method of inducing a mucosal immune response in a subject, comprising administering to the mucosa of the subject an amount of antigen-encoding DNA effective to induce a mucosal immune response complexed to a transfection-facilitating lipospermine or a lipospermidine. In the method of inducing a mucosal immune response, the antigen-encoding DNA can encode an antigen that is expressed on the surface of infected cells during the course of infection. The present method should apply to all mucosally acquired pathogens in which expression of antigen on the surface of a mucosal cell mimics natural infection. DNA encoding the envelope glycoproteins of viral pathogens is the rational choice for use in the present method.

Lipospermines and lipospermidines are bifunctional molecules consisting of one or more hydrophobic chains covalently linked to a cationic grouping in which there is coordination of three or more amide hydrogens with a phosphate oxygen of the DNA chain forming an ionic charge complex. One preferred example of a lipospermine is DOGS (dioctadecylamidoglycylspermine). Diotadecylamidoglycylspermidine is another likely candidate, because it has the same structure as DOGS, but lacks one of the two arms having two non-essential cationic charges.

The invention also provides a composition, comprising an amount of DNA encoding an envelope antigen or envelope-associated antigen of a pathogen complexed to a lipospermine. More specifically, the invention provides a composition, comprising an amount of DNA encoding an envelope antigen of HIV complexed to a lipospermine

DETAILED DESCRIPTION OF THE INVENTION

Figure 1:
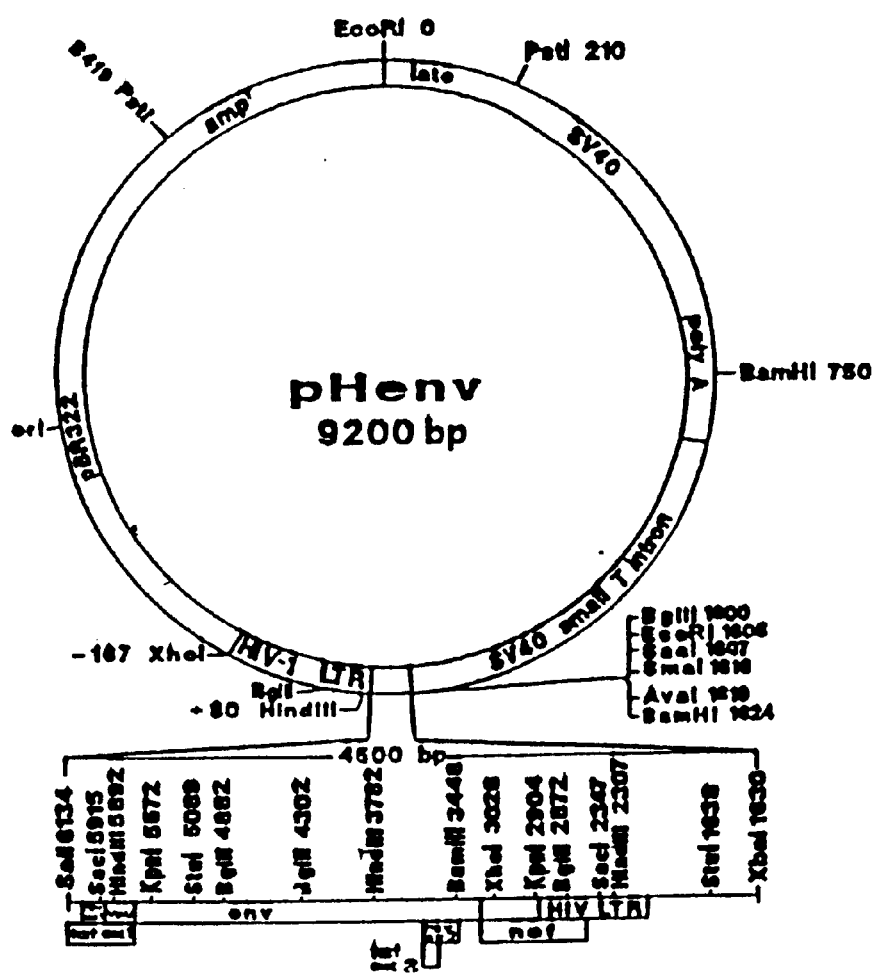
FIG. 1 shows a circular map of pHenv showing HIVenv insert between 5' and 3' LTRs. Rev is functional in this construct.

The invention provides a method of inducing a mucosal immune response in a subject, comprising administering to the mucosa of the subject an amount of antigen-encoding DNA effective to induce a mucosal immune response complexed to a transfection-facilitating lipospermine or a lipospermidine.

The invention is applicable to pathogens generally, because expression of the pathogen antigen encoded by the antigen-encoding DNA results in exposure of the pathogen antigen on the surface of the cell, mimicking either a portion of the replicative cycle of the pathogen or the initial attachment of the pathogen to the cell surface. Examples of viral pathogens include, but are not limited to, retroviruses (human immunodeficiency viruses), herpesviruses (herpes simplex virus; Epstein Barr virus; varicella zoster virus), orthomyxoviruses (influenza), paramyxoviruses (measles virus; mumps virus; respiratory syncytial virus), picornaviruses (Coxsackie viruses; rhinoviruses), hepatitis viruses (hepatitis C), bunyaviruses (hantavirus; Rift Valley fever virus), arenaviruses (Lassa fever virus), flaviviruses (dengue fever virus; yellow fever virus; chikungunya virus) and coronaviruses, among others. Examples of bacterial pathogens include, but are not limited to, species of the following genera: Salmonella, Shigella, Chlamydia, Helicobacter, Yersinia, Bordatella, Pseudomonas, Neisseria, Vibrio and Haemophilus, among others.

Antigen-Encoding DNA

In the method of inducing, a mucosal immune response, the antigen-encoding DNA can encode an antigen that is expressed on the surface of infected cells during the course of infection. The present method should apply to all mucosally acquired pathogens in which expression of antigen on the surface of a mucosal cell mimics natural infection. Because the primary immune response to bacteria is to a relatively small number of cell surface antigens, the process for selecting antigen-encoding DNA for bacterial pathogens is similarly routine. For example, the major bacterial immunogens are epitopes on surface structures (191). There are numerous examples of viral antigens in which this is expected to be the case. It is expected that antigens of other microbiological pathogens will share this characteristic. As used herein, an antigen is a molecule that elicits an immune response.

DNA encoding the envelope glycoproteins (e.g., gp160 HIV or its cleaved derivative proteins, gp41 and gp120) of viral pathogens is the rational choice for use in the present method. Envelope-associated-proteins, such as gp17 are also reasonable choices, because of their presentation on the cell surface of infected cells. A reasonable terminology to define a subset of antigens that will be effective in this method is "envelope and envelope-associated proteins." Specific epitopes of these proteins that elicit an immune response in a subject can be selected by routine methods, including epitope mapping and analysis of conformational dependency. Particularly, epitopes that elicit neutralizing antibodies are important bases of the present method. DNA encoding these antigens can be obtained by cloning and synthesis methods known in the art and further described below.

For example, the antigen-encoding DNA can encode an antigen of a human immunodeficiency virus. As a more specific example, the antigen-encoding DNA can encode a human immunodeficiency virus envelope glycoprotein. Although the envelope antigens are expected to be the main inducers of antibodies and cytotoxic lymphocytes (CTLs), there is literature evidence of CTLs against the gag (i.e. internal antigen) of HIV. The preferred antigen-encoding DNAs include gp160, gp120 and gp41 separately expressed (i.e., gp160 is normally cleaved by a host protease to gp120 and gp41). DNA encoding gp17, which is one of the gag proteins that is attached by a myristylation link to: the envelope, and for which there is literature evidence for a neutralizing antibody epitope close to the myristylation site, can also be included. The antigen encoding DNA can encode antigenic fragments of the envelope and envelope-associated proteins, for example, the V3 loop of a human immunodeficiency virus envelope glycoprotein gene.

An antigen-encoding DNA will need to have a start codon, a stop codon and a membrane anchor. Thus, if these are not present, or in order to optimize the present method, it is,expected that the sequences of antigen encoding DNA will be mutated in one or more ways to preserve or enhance the antigenicity of the expressed antigen. For example, a mutation of the gp160 cleavage site can be made to keep the protein uncleaved. A stop signal has to be generated for gp120 as well as a membrane anchor. In addition, the known antibody enhancing domain of gp41 will be removed for both HIV and RSV as described in detail in the Examples. Numerous versions of the V3 region of the envelope glycoprotein can be made to reflect the major quasispecies found in viral isolates. These can then be administered in multiple genetic constructs, each containing a single transcribed ORF, or in a single or a few genetic constructs, each containing multiple transcribed ORFs. Genetic manipulations of this nature are known in the art (188) and specific examples described in the Examples.

Briefly, mutations are produced using the p-Alter-1 kit from Promega, which incorporates antibiotic selection for selection of the desired mutations. It necessary to use the ssDNA template procedure for reliable generation of desired mutations. A critical change from the kit protocol is the generation of our own helper phage ssDNA. The ss Phage DNA isolation kit and procedure from Biolabs, Inc. is used for the production of pure ssDNA. Another critical change is the substitution of the ES 1301 mutS *E. coli* supplied with the kit with XL mutS *E. coli* from Stratagene for transformation. DH5α a *E. coli* for which the subject mutS mutations have been generated have also been successfully used. The latter are devoid of repair enzymes. The components of the above method are generally applicable to DNA encoding other antigens.

Examples of gene engineering that are expected to be incorporated into a plasmid containing, for example, the HIV envelope for eukaryote cell transfection and antigen expression on the surface of the cell include: 1) elimination of the HIV LTR control elements and placement under a more powerful promoter such as CMV, 2) elimination of the gp160 proteolytic cleavage site so that gp120 does not disassociate from the membrane anchored gp41, 3); conversion of the RRE present in the 5' end of gp41 and which forms extensive secondary structure to a linear structure by the introducing of silent mutations with no changes in the amino acid sequences of the product and 4) the elimination of the primary enhancing domain by point or deletion mutations which destroy this capacity. Examples of these mutations are further described in the Examples. Although, specific mutations for HIV envelope glycoproteins are given, it is understood that the same considerations for the generation of an efficient immunization construct apply to the generation of a construct using an antigen-encoding DNA for a different antigen.

The vectors used in the present method can include promoters and regulatory sequences that are relevant to the antigen-encoding DNA. Typically, the vector must be a eukaryotic vector that is capable of replication in *E. coli*. The preferred vector contains a bacterial origin of replication, an antibiotic resistance selection gene, eukaryotic promoter and a polyadenylation gene. As clearly demonstrated in the Examples, other vectors can be designed by the skilled artisan that do not share all of the above characteristics, yet permit transfection.

Lipospermine/Lipospermidine

The transfection-facilitating lipospermines and lipospermidines used in the methods are bifunctional molecules consisting of one or more hydrophobic chains covalently linked to a cationic grouping in which there is coordination of three or more amide hydrogens with a phosphate oxygen of the DNA chain forming an ionic charge complex. To facilitate transfection, the lipospermines\lipospermidines can both protect the DNA and make it appear more hydrophobic to the cell membrane of the cell to be transfected. For example, the charge interaction positions the hydrophobic arms along the major or minor groove of DNA (see Examples) provide a hydrophobic covering for the highly charged DNA macromolecule and affords facilitated cellular entry by association of the hydrophobic surface covering DNA with the hydrophobic component of the plasma membrane of the cell. Based upon molecular modeling using DOGS, it appears that the amino hydrogen of the peptide bond and adjacent amide hydrogens all coordinate on one phosphate oxygen (i.e., 1.91 to 2.0 Å distance). The other two amide hydrogens are useless. Thus, the use of spermidine in the construction of the complexing agent might be more effective.

One preferred example of a lipospermine is DOGS (dioctadecylamidoglycylspermine). Diotadecylamidoglycylspermidine is another likely candidate, because it has the same structure as DOGS, but lacks one of the two arms having two non-essential cationic charges. Additionally, lipospermines or lipospermidines having hydrophobic chains of 8 to 20 carbons could also be expected to interact similarly with the major and minor grooves of the DNA. Although less preferred, the lipospermine or lipospermidine could have a single hydrophobic side chain (e.g., monooctyl, monooctadecyl, monododecyl, etc.).

The preferred molar cationic ratio of the lipospermine to DNA is about 5:1. Alternatively, the lipospermine can be complexed to DNA in a molar cationic ratio ranging from about 2 to about 10. Because the ionic interactions between the lipospermine/lipospermidine and the DNA will be the same regardless of the antigen encoded, the present teaching with regard to the formulation of DNA-lipospermine/lipospermidine complexes is applicable to the antigen-encoding DNAs of the invention.

Thus, the invention also provides a composition, comprising an amount of DNA encoding an envelope antigen or envelope-associated antigen of a pathogen complexed to a lipospermine. More specifically, the invention provides a composition, comprising an amount of DNA encoding an envelope antigen of HIV complexed to a lipospermine. The DNA in the plasmid described in the Examples. As described above the antigen-encoding DNA of the invention can encode any antigen that is presented on the surface of host cells during infection or on the surface of the pathogen and exposed to the host immune system. Examples of such antigens are described in virology textbooks (see for example *Fundamental Virology*, 2nd. Ed., pp373–375 (189)).

In the method of inducing a mucosal immune response, the antigen-encoding DNA can also be administered without the aide of a complexing molecule. For example, the DNA can be bolistically administered, along with an activated form of vitamin D3 as described in the Examples. Briefly, the DNA is complexed to gold particles and delivered to skin cells by propelling them through plasma membranes using a helium propellant. The activated form of vitamin D3 can be delivered to the same cells by inclusion in the gold suspension containing the naked DNA and propelled into the cells by the same means. The activated vitamin D3 can, alternatively, be delivered to the transfected skin cells by topical application in a solvent carrier, such as dimethyl sulfoxide. In this manner, the skin can act as a mucosal surrogate in terms of the ability to induce mucosal immunity.

The Mucosal Immune System

Significant indirect evidence indicates the presence of a common mucosal immune system (47,50). Induction of mucosal immunity in bronchus-associated lymphoid tissues usually yields evidence of immunity in gut-associated lymphoid tissues. The common element is the generation of mobile IgA secreting plasma cells with an affinity for mucosal-associated lymphoid tissues of various types.

The mechanism of selective transport, of J-chain-containing polymeric IgA (pIgA) through an epithelial cell to the mucosal surface has been determined. Briefly, pIgA assembled in subepithelial plasma cells from monomeric IgA (mIgA) with the participation of J chain, interacts with the membrane form of secretory component (SC). The pIgA-SC complex is internalized in endoplasmic vesicles which fuse with the apical membrane, and S-IgA is released into the external secretion. See Reference 42.

Although IgG can be found on mucosal surfaces following mucosal immunizations, IgA is the predominant Ig in mucosal immunity. This is secondary to the presence of an Ig receptor with greatest affinity for pIgA. This receptor is expressed on the surface of mucosal epithelial cells and actively transports pIgA to the mucosal surface (47–49) through mucosal epithelial cells.

Mucosal Administration

In the method of inducing a mucosal immune response, the antigen-encoding DNA is administered to the mucosa of the subject. Thus, specific examples of the mucosal administration include nasal, oral, rectal and vaginal. Nasal administration can be by nasal aerosol spray (see Examples) or nebulizer among other well practiced methods. Rectal and vaginal administration can be by a variety of: methods, including lavage (douches, enemas, etc.), suppositories, creams, gels, etc. For nasal administration, an aerosol spray or nebulizer can be used.

Depending on the intended mode of administration, the compounds of the present invention can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the DNA and, in addition, may include other medicinal agents, pharmaceutical agents, carriers, adjuvants, diluents, etc. By "pharmaceutically acceptable" is meant a material that is not biologically orotherwise undesirable, i.e., the material may be administered to an individual along with the selected compound without causing any undesirable biological effects or interacting in a deleterious manner with any of the other components of the pharmaceutical composition in which it is contained.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated. Actual methods of preparing such dosage forms are known, or will be apparent, to those skilled in this art; for example, see *Remington's Pharmaceutical Sciences* (190).

In the present method, the DNA is complexed to lipospermine and is administered to the subject as a single primary vaccination followed by one or more booster vaccinations at three week to three month intervals. Routine optimization of this administration regimen can be made using routine optimization procedures.

The exact amount of DNA required will vary from subject to subject, depending on the age, weight and general condition of the subject, the particular formulation used, its mode of administration, and the like. Thus, it is not possible to specify an exact amount. However, an appropriate amount may be determined by one of ordinary skill in the art using only routine experimentation given the teachings herein. Thus, the amount of DNA administered can be any effective amount. There should be little difference in a human immunizing dose vs. mouse dose, because there is no reason to expect that human cells are more or less susceptible to transfection than mouse cells. Typically, the preferred amount of DNA required for effective transfection is from about 10 ng to 10 $\mu$g. Variations in the transfection efficiency between humans and mice can be accommodated by routine adjustments in the dosage. For example, the. amount can range from 1.0 ng to 1 mg. Anything over 10 $\mu$g DNA becomes logistically difficult to handle and increases the risk of toxicity and is impractical.

The following examples intended to illustrate, but not limit, the invention. While the protocols described are applied in the context of HIV immunization, they have applicability with other pathogens by virtue of their shared mucosal infection mechanisms. While the protocols described are typical of those that might be used, other procedures known to those skilled in the art may be alternatively employed.

EXAMPLES

Genetic Immunization

The ability to simulate-viral replication by transfection of non-replicating, transcription/translation-permissive viral DNA encoding viral proteins essential for a protective immune response by the host provides the advantages of an attenuated, live vaccine without the potential for reversion to virulence.

Genetic immunization offers unique advantages to the vaccine field. DNA is easy to prepare and manipulate. A variety of eukaryotic promoters, signal sequences, and hydrophobic anchors can be constructed to maximize immune responses. Advantageous site-directed mutations are relatively easy to achieve. DNA is stable and requires no refrigeration in the field during mass population vaccinations. Genetic immunization produces both humoral and cellular immune responses similar to attenuated microorganisms. The most important advantage for an HIV vaccine, however, is the relatively easy formulation of multiple sequence variations in a single genetic immunization, each of which will normally be expressed on the cell surface with the development of a wide repertoire of protective responses. The major disadvantage has been the relative massive quantities of DNA required.

HIV Phenotypic Expression

Primary infection of a naive host by HIV-1 results in a variable clinical course (177). In the majority of cases (50–70%) an acute clinical syndrome of malaise and fever lasting 1–2 weeks associated with viremia occurs some 2–4 weeks following exposure (163–164). In a minority of patients this acute phase of infection is subclinical. Although occasional primary infections progress to AIDS very rapidly (65), most patients enter an asymptomatic phase with a subsequent variable progression to AIDS after 1 to more than 10 years (166). Presumably this initial viremic phase is controlled by an effective immune response against the initial infecting viral genotype (171). If the initial viremic phase is initially controlled by host defense mechanisms, the question remains why the virus eventually gains the upper hand over the initially effective humoral and cellular defense mechanism.

One of the striking characteristics of HIV is its mutability especially in the viral envelope of glycoproteins, gp120 and gp41. The high mutation rate in HIV is believed to be a function of the high error rate by reverse transcriptase in the conversion of viral 70S ss RNA into ds proviral DNA (estimated at 2errors per viral copy). This high mutation rate is sugqestive of a potential for phenotypic expression variants which may explain, in part, the high degree of interindividual variability to HIV infection.

A preponderance of data indicates that most primary infections by HIV-1 have a non-syncytial inducing. (NSI) phenotype (i.e., monocytotrophic virus unable to form, syncytia in allogenic primary co-culture or in T-cell indicator cells) in contrast to the syncytial inducing (SI) phenotype found with increasing frequency with disease progression (163–170). Ho and his colleagues (171) have carefully examined specific sequences from gp120, gp41, nef, and p17 using cloned PCR amplified DNA from PBMCs of five seroconvertors and two sexual partners. As expected the HIV transmitters exhibited substantial HIV sequence heterogeneity while there was marked HIV sequence homogeneity from the recent seroconvertors which corresponded to minor species in the transmitters. Surprisingly gp120 exhibited the greatest sequence homogeneity (>99% similarity). Although these data need to be reproduced in multiple studies, they suggest that HIV infection is much more sequence restricted at least for sexual transmission than ever considered previously. Secondly, they suggest that the phenotypic expression of acquired genomic variation is responsible at least in part for the varied clinical progression of HIV disease although secondary HIV infection cannot be excluded as the. source of genomic variability during disease progression.

One expression of acquired genomic variation is the conversion of primary HIV-1 isolates from NSI, monocytotropic to SI, T-cell line permissive variants (i.e., virtually all isolates can replicate in PBMCs but only SI isolates replicate in T-cell lines). The primary determinant for this functional (NSV vs SI) tropism (monocytotropic vs T-cell line permissive) is the third variable domain (V3 loop) of gp120, a glycoprotein of HIV-1 which is fully exposed on the viral surface (172). The V3 loop is a disulfide-linked polypeptide composed of 34–37 amino acids with a conserved tetrad GPGR motif midway in its sequence (173). The remainder of the sequence is highly variable and has been identified as a fusion domain of gp120 (55). Another lab (175, 176) has demonstrated that amino acid sequence changes in the V3 loop which reduced cleavage by several serine proteases conferred the NSI functional phenotype on viral recombinant vaccinia viruses expressing HIV-1 envelope sequences. These V3 loop amino acid variations determining SI vs NSI functional phenotype are illustrated in Table 1.

Functional Immune Responses to HIV

An important concept that is frequently dismissed in considering the design of an HIV vaccine is that both protective and adverse immune responses can be generated by the virus or its envelope component.

1. Neutralization of HIV

Over the past 5 years, a number of HIV-neutralizing epitopes (an epitope being defined as the minimum number of amino acid residues, either linear or conformational, that can be bound by an antibody) or domains (regions containing a cluster of epitopes) have been identified, including one within the p17 gag protein (51) and many within the gp160 envelope protein. These domains are summarized in Table 2 with respect to the specific sequence identified (amino acid residues within designated. peptides being numbered according to the Los Alamos database (52)), the specificity of the neutralizing response, the relative immunogenicity of the domain, and. the role of these antibodies in blocking CD4 receptor binding. Several domains have been identified by immunizing animals with synthetic peptides and testing the hyperimmune serum for the ability to neutralize HIV-1 in vitro. By this method, residues 247–267 (53), 296–331 (54–59), 451–477 (54) and 496–525 (60) within gp120, and residues 593–604 (61), 609–625 (54) and 721–745 (54, 60, 62) within gp41 have all been reported to stimulate the production of HIV-neutralizing antibodies in experimental animals. However, investigators have had some difficulty in determining what constitutes a significant neutralizing response, since several of these peptides only stimulated antibodies that could neutralize HIV-1 to a titer of 1:4 or 1:8 (54). Similarly, the antibody effect on gp120 binding to the CD4 receptor is of significant interest. Only two domains have been examined, however. Antibodies to the second conserved domain (domain 1 of Table 2) have no effect on binding (53), while antibodies to the recognized CD4 receptor-binding domain effectively inhibit binding (63).

There is also evidence confirming the presence of antibodies that neutralize. HIV in the serum from HIV-infected people and chimpanzees. The vast majority of reports concern antibody to the V3 loop (residues 296–331) (57,58,64, 65). These antibodies have been shown to be responsible for the type-specific neutralizing response to HIV-1. Type-specific antibodies neutralize one strain (i.e. $HIV_{IIIB}$, $HIV_{MN}$, $HIV_{RF}$, etc.) while group-specific antibodies neutralize more than one strain. The region is hypervariable yet contains a highly conserved Arg-Gly-Pro-Gly-Arg sequence at residues 311–315 (66). Immune responses to the V3 loop are complicated by the hypervariable sides of the loop

TABLE 1

Relationship of HIV phenotypic syncytium expression and the amino acid sequence of the V3 loop[a]

| HIV Strain | Tropism | Syncytium Phenotype | V3 loop amino acid sequence |
|---|---|---|---|
| $IIIB_{wt}$ | T-cell | SI | 263        280  255 287    297 |
| [b]$IIIB_{m4}$ | T-cell/Partial Monocyte | SI | CTRPNNNTRKRIRIQRGPGRAFVTIGKINM RQAHC<br>                                                E |
| ADA | Monocyto- | NSI | SH   Y T E IGDI |
| YU2 | Monocyto- | NSI | SN   LY T E IGDI |

[a]Data from envelope recombinants in vaccinia vectors (175, 176).
[b]Site directed mutagenesis at #287 KEE.

(residues 296–309 and 317–333). It seems that much of the antibody to the loop is concentrated against the hypervariable regions, and therefore the antibody response to the loop is type specific (67–71). $HIV_{MN}$ is the most universally recognized strain of HIV in North America with respect to the frequency of HIV-infected subjects with neutralizing activity towards $HIV_{MN}$ and the geometric mean titer of all sera against $HIV_{MN}$ (72). Although the dominant antibody response is type-specific against linear epitopes, these findings suggest that there may be some group-specific neutralizing response to the $HIV_{MN}$V3 loop, perhaps to conformational epitopes involving the conserved sequence at residues 311–315. Using her extensive repertoire of human mAbs to the V3 loop, Zolla-Pazner convincingly argues for conformational influence on binding to infectious virus. Her data blunt the distinction between group- and type-specific neutralization. The role of the V3 loop antibodies in HIV infection is discussed in greater detail later. One disturbing complication with the V3 findings is the emergence of anti-V3-loop-resistant viruses following in vitro treatment of HIV with neutralizing anti-V3-loop monoclonal or polyclonal antibody. Mutations can occur both within (73–76) and outside the V3 loop (77,78). Indeed, it has been shown that HIV-infected subjects can develop variants that resist previous isolate-specific neutralization (79). One non-V3-loop mutant has been sequenced, and the only change in the amino acid sequence of the envelope glycoprotein was a substitution of threonine for alanine at residue 582 (78), a region not only outside the V3 loop but residing in the amino-terminal region of gp41. It has been convincingly shown that this immune-selected point mutation is not part of a specific neutralization epitope (80). Therefore, other regions of the envelope may interact with the V3 loop, thus complicating the development of a vaccine. In vivo neutralization-escape mutants have also been described in HIV-infected chimpanzees (81), where non V3-loop mutations were responsible for the escape from HIV-neutralizing antibodies. Group-specific neutralization of HIV infection has been demonstrated in several laboratories (82–86). These group-specific antibodies may block infection via CD4 or some alternative HIV receptor (87–89).

An intriguing aspect of the analysis of neutralizing antibody domains is the recognition that relative immunogenicity as a result of natural infection, versus the experimental induction via synthetic peptides linked to a carrier, is frequently divergent (Table 2). The immunodominant regions of gp120 and gp41, which induce large quantities of antibody, are relatively weak as experimental immunogens, while those of gp120 that induce relatively little antibody during a natural infection are strong inducers of antibody when coupled to a carrier. This suggests,the presence of alternative routes of antigen processing between infection and that produced by recombinant viral proteins or synthetic peptide immunogens, which may be important in the design of vaccines. Since genetic mucosal immunization mimics viral infection, it is more likely that functional immune responses will more accurately reflect those from de novo HIV infection.

The identification of neutralizing domains has also been made easier by the production of monoclonal antibodies (mAbs) against the HIV. Several anti-V3 loop mAbs have been produced that neutralize a specific virus isolate (91, 92, 108, 109) as well as one mAb which also mediates cellular cytotoxicity (90). These include a number of murine mAbs (mu-mAbs) (108,109) and several human mAbs (hu-mAbs) (91,92). Several neutralizing monoclonal antibodies to other regions of the HIV envelope have also been described, including amino acid residues 423–437 (63), residues 728–745 (186) and the CD4+ binding domain (91). Several additional neutralizing mAbs have been shown to bind to HIV envelope glycoproteins (92,93). One of four mAbs had neutralizing activity and bound to gp41 (92). Furthermore, a report by Hansen et al. (94) indicates that mAbs directed against three different carbohydrate moieties, either N- or O-linked, were able to neutralize both $HIV_{IIIB}$ or a patient isolate in vitro. A study by Müller et al. (95) demonstrated that polyclonal antiserum against yeast mannan inhibited HIV replication. The importance of virus glycosylation in HIV infectivity has been reported previously by several laboratories (96–106). Thus, simple inhibition of functional glycosyl groups could explain the neutralization effects by antiglycosyl antibodies (94,95). Other data, however, suggest that secondary and tertiary structures of the envelope glycoproteins are of significant importance in the generation of group-specific rather than type-specific neutralizing antibodies. A requirement for carbohydrate in the group-specific neutralization of HIV has been demonstrated by comparing antibodies raised against a glycosylated versus a non-glycosylated gp120 (107), and by comparing the specificity of neutralization by serum eluted from non-glycosylated gp120 (108). In both cases carbohydrate was required for group-specific but not type-specific neutralization of HIV. Moreover, a recent report demonstrates that elimination of all five variable regions with retention of disulfide bonds in a non-glycosylated recombinant HIV produces an immunogen that is incapable of generating neutralizing antibodies (107). Thus, it is not known whether antibodies block specific function by blocking carbohydrate binding or whether they inhibit by disrupting native secondary and tertiary conformations required for infectivity. The locations of N-linked carbohydrate structures were studeid with respect to their linear relationship to known functional antibody domains on gp120 and gp41 as well as epitopes recognized by CD8+ and CD4+ CTLs from HIV seronegative rHIV vaccines (20).

TABLE 2

Neutralizing Regions of the HIV-1 Envelope Glycoproteins and p17 Protein.

| Do-main | Identifying synonym | Sequence (No.-No.)* | Nuetral-ization speci-ficity | Method | Blocks gp120 binding to CD4 | Immunogenicity Natural infection | Experi-mental induction | References |
|---|---|---|---|---|---|---|---|---|
| 1 | Second conserved domain | CTHGIRPVVSTQLLLNGSLAE (247–267) | Group specific | Animals | – | + | +++ | (53) |

TABLE 2-continued

Neutralizing Regions of the HIV-1 Envelope Glycoproteins and p17 Protein.

| Domain | Identifying synonym | Sequence (No.-No.)* | Neutralization specificity | Method | Blocks gp120 binding to CD4 | Immunogenicity Natural infection | Experimental induction | References |
|---|---|---|---|---|---|---|---|---|
| 2 | V3 loop | CTRPNNNTRKRI RIQRGPGRAFVTIGK IGNMRQAHC§ (296–331) | Type-specific | Animals, humans/mAb | ND | + | +++++ | ?? |
| 3 | CD4 receptor binding domain | IINMWQKVGKAMYAP (423–437) | Group-specific | mAb | + | ± | +++ | (63,91) |
| 4 | — | GLLLTRDGGNSNNESEIFRLGGGD (451–474) | ND | Animals | ND | ? | ± | (54) |
| 5 | gp120 immunodom. region | VAPTKAKRRVVQREKRAVGIGALFLGFLGA** (496–525) | Group-specific | Animals | ND | ++++ | ++ | (60) |
| 6 | gp41 immunodom. region | LGLWGCSGKLIC (593–604) | ND | Animals | ND | ++++ | + | −61 |
| 7 | gp41 second immunodom region | PWNASWSNKSLEQIWNH (609–625) | ND | Animals | ND | +++ | ++ | (54) |
| 8 | gp41 post-membr. span | DRPEGIEEGGERDRDRS (728–745) | Group-specific | Animals/mAb | ND | + | ++ | (54,60,62, 63,90) |
| 9 | Myrstyl p17 | ELDRWEKIRLR (12–22) | ND | mAb | ND | ? | +++ | (51) |

Immunodom. immunodominant;
post-member. post-membrane;
ND not determined
mAB monoclonal antibody.
*Sequence shown is the H x B2 clone of the IIIB strain as reported in the Los Alamos database (52). Numbering is based on the first methionine open reading frame as amino acid number 1 at nucleotide 6224 for envelope neutralizing domains and nucleotide 789 for the p17 neutralizing domain. Disulfide bonds in domains 2 and 6 are indicated by connecting lines. Specificity of neutralization is cited where there is direct experimental evidence; where no evidence isavailable, group-specific responses are likely where there is conversion of the sequence between various viral isolates. Best evidence where conflicting data have been reported.
§Principal domain of V3 loop is shown in bold.
**Peptide tested actually spans gp120/gp41 peptide hydrolysis site on gp160 as indicated by the arrow (66).

2. Antibody-dependent enhancement of HIV

Antibodies that enhance viral infectivity have been described for a number of viruses (112–126). The most frequently cited example involves enhancement of dengue virus infection (112–115). Results indicate, that non-neutralizing antibodies can actually increase the number of infectious virions in vitro by binding virus to Fc receptors on monocytes and macrophages (118). In dengue infection, the degree of enhancing-antibody-present roughly correlates with disease severity (113). In addition to this Fc receptor-mediated mechanism, it has been shown that enhancement of infection by a flavivirus, West Nile virus, can be mediated by complement and complement receptors on cells (119). Enhancement has been demonstrated in vitro for a number of viruses including flaviviruses (116–122), alphaviruses (123), rabies virus (124), Sindbis virus (125), and coronavirus (126). There is some evidence for in vivo enhancement of several other viruses where ineffective vaccination resulted in increased severity of disease. The most notable of these examples occurred in children immunized against; respiratory syncytial virus (RSV) (127–130) or cotton rats immunized against RSV (131). Other examples include an inactivated measles vaccine (132,133), and possibly an ineffective caprine arthritis and encephalitis virus vaccine although the more severe arthritis following vaccination could have been due to antigen-antibody complex formation (134,135).

Lentivirus enhancing antibodies were first described for HIV infection in 1987 (110). Subsequent reports have identified two mechanisms for enhancement that function in vitro. The first involves antibody to HIV in combination with complement proteins (157,158) and requires cells that bear both CD4 and complement receptor type 2 (CR2) (139). The second mechanism requires antibody to HIV and cells bearing Fc receptors (140). Since the Fc mechanism generally has only a twofold enhancement versus >100 fold for complement-mediated antibody dependent enhancement (C'-ADE), the present research focuses on the latter phenomenon.

For C'-ADE, it is known that the HIV envelope. glycoproteins can activate complement and that antibody to HIV leads to increased fixation of complement component C3 on HIV or HIV-infected cells (141). This complement can bind HIV to CR2 and act to increase the amount of HIV in proximity to CD4+cell surfaces resulting in a greater likelihood that the gp120 would interact with the CD4 receptor which mediates the entrance of HIV into the cell. Spear and his colleagues have directly shown that C'-ADE results in increased HIV binding to target cells and an increased integrated proviral copy number (141). Moreover, this group has shown that 30% of CD4 lymphocytes bear the CR2 receptor and that this CD4/CR2 lymphocyte is preferentially selected during the early phases of CD4 cell decline as a function of HIV infection (142).

With the production of huMAbs against the HIV-1 envelope glycoprotein, it became possible to separate virus neutralization from enhancement. It was shown that several huMAbs against the HIV-1 envelope glycoproteins could enhance HIV-1 infection but did not neutralize HIV-1 in vitro (143). The ability of the huMAbs to enhance infection was not determined by the ability of the huMAbs to activate complement nor by the IgG subclass of the huMAbs (143, 144). These enhancing huMAbs have been mapped to linear domains in the HIV-1 gp41 transmembrane glycoprotein. Of six enhancing huMAb identified to date, five map to amino acid residues 579–613 (144,145), the primary immunodominant domain of gp41 (146–148). One of the six maps to another immunodominant domain (143,145). These results suggest that there are only a few enhancing domains in the envelope of HIV-1 and that these domains are conserved, immunodominant regions of the HIV-1 envelope. Recently extended these observations have been extended to SIV by demonstrating that the TM protein region homologous with the first and primary enhancing domain of HIV has similar capacity to induce the formation of enhancing antibodies (150). The data show in vivo that preimmunization with a synthetic peptide (aa 603–622) from $SIV_{mac251}$ stimulated the production of antibodies which suppressed the beneficial effects of recombinant gp60 SIV vaccine and appeared to enhance SIV infection (150). There is further evidence from several lentivirus vaccines that suggests that the humoral response to envelope glycoproteins may be detrimental to the host. For example, SIV envelope glycoprotein recombinant vaccines have, for the most part, failed to protect monkeys from subsequent virus challenge (151,152), while similar envelope-based recombinant vaccines for HIV have been largely ineffective in preventing HIV infection of chimpanzees (153–155). In equine infectious anemia virus (EIAV), a baculovirus recombinant envelope glycoprotein vaccine apparently led to worse disease in horses subsequently challenged with EIAV (156). Recently, Gardner et al. (157) reported that passive immunization of rhesus macaques by serum from SIV-infected rhesus macaques led to an apparently enhanced course of disease with five of six such animals dying within 6 months of challenge. In that study, there was a direct correlation between failure of passive immunization and higher antibody levels against the aa 603–622 peptide by ELISA (158). These data differ from passive immunization experiments reported by Putkonen et al. (159) for SIV and in the feline. immunodeficiency (FIV) model (160), although investigators have reported enhanced infections for FIV in vitro (161) and similar passive immunization failure for $SIV_{mac}$ (162) in vivo. It is, therefore, prudent to consider the potential for enhancement in all vaccine preparations. Although HIV and SIV enhancement is relatively weak in comparison to Dengue, it may mean the difference between success or failure to protect vaccine recipients (150).

Induction of Mucosal Immune Responses In Vivo

The transfection DNA used as the genetic immunogen was pHenv, a 9600 bp pBR322-based plasmid containing the entire HIV-1 envelope genome, functional tat and rev transactivator sequences and corresponding LTR TAR and RRE sequences, obtained originally from the NIH AIDS Reference Program. FIG. 1 details the circular plasmid map. This plasmid on transfection has been shown to efficiently express the env proteins of HIV- $1_{pNL4-3}$ resulting, in extensive cell fusion with cells expressing CD4 (180). pACYC177 was used as an irrelevant DNA control immunogen. Plasmids were produced in. *E. coli* JM109 grown in LB broth containing 50 μg/ml ampicillin and cells harvested at $OD_{600nm}$=0.50. DNA was harvested from cell pellets using an SDS lysis procedure with purification on Magic Prep columns (Promega Corp.). Plasmid DNA was eluted at 70° C. with TE buffer and precipitated at −70° C. in 0.1 M Na acetate, pH 5.2. Purified plasmid DNA was examined by size in agarose electrophoresis gels for known restriction endonuclease hydrolysis sites pHenv DNA was consistent with a 9600 bp DNA containing four HindIII sites producing 3708, 5818, 7293, and 9520 bp, fragments and two XhoI sites producing 6625 and 7965 bp fragments. The 3940 bp control plasmid, pACYC177, contains one BamHI site and two StaI fragments of 965, bp and 2305 bp. Concentrations of DNAs were based on OD\|a\|al(50 μg, 260 nm\|, 1 cm )=1.

Animals

Five- to six-week-old female Balb/c mice from Harlan industries were randomly sorted into groups of five mice each. The groups were arranged into three classes of DNA immunization plus irrelevant DNA immunogen and naive animal controls. Table 3 details the route of immunization, composition of immunogen, dose, number of immunizations, and total DNA dose exposure. Table 4 summarizes the antibody responses detected in the serum of mice as the result of transfection with DNA containing transcription competent HIV-1 env sequences. Naked DNA (100 μg) yielded HIV-specific serum, IgG responses in 2 of 5 animals with a single IM exposure and 3 of 5 animals with 2 or 3 IM exposures. Naked DNA (10 μg) produced HIV-specific responses in 40% of the animals with one, two, or three IM exposures. Naked DNA (1 μg) produced no HIV-specific immune responses with IM exposure. The highest average IgG titer occurred in the 10 μg per exposure group. DNA (10 μg or 1 μg) complexed with dioctadecylamidoglycylspermine (DOGS) produced HIV-specific immune responses in 80% of IM-treated animals after one, two, or three exposures with the highest average titer occurring in the group receiving three exposures. Aerosol exposure to 10 μg DNA complexed with DOGS produced systemic HIV-specific immune responses in 20% of mice with one exposure and 40% of mice exposed two or three times. Aerosols with 1 μg DNA complex produced HIV-specific IgG responses in 20% of mice after one or two exposures and 80% of mice following the third exposure with an average titer of 1:850.

Table 3 shows results of a mucosal administration.

TABLE 3

DNA immunization schedule in 5- to 6-week-old female Balb/c mice. Exposure to immunogens every three weeks.

| Group # | Immunogen | Route of Immunization | Number of Immunizations | DNA/ Immunization | Total DNA |
|---|---|---|---|---|---|
| 1 | Naked DNAenv | IM | 1 | 100 μg | 100 μg |
| 2 | Naked DNAenv | IM | 2 | 100 μg | 200 μg |
| 3 | Naked DNAenv | IM | 3 | 100 μg | 300 μg |

TABLE 3-continued

DNA immunization schedule in 5- to 6-week-old female Balb/c mice. Exposure to immunogens every three weeks.

| Group # | Immunogen | Route of Immunization | Number of Immunizations | DNA/Immunization | Total DNA |
|---|---|---|---|---|---|
| 4 | Naked DNAenv | IM | 1 | 10 µg | 10 µgg |
| 5 | Naked DNAenv | IM | 2 | 10 µg | 20 µg |
| 6 | Naked DNAenv | IM | 3 | 10 µg | 30 µg |
| 7 | Naked DNAenv | IM | 1 | 1 µg | 1 µg |
| 8 | Naked DNAenv | IM | 2 | 1 µg | 2 µg |
| 9 | Naked DNAenv | IM | 3 | 1 µg | 3 µg |
| 10 | DOGS:DNAenv complex | IM | 1 | 10 µg | 10 µg |
| 11 | DOGS:DNAenv complex | IM | 2 | 10 µg | 20 µg |
| 12 | DOGS:DNAenv complex | IM | 3 | 10 µg | 30 µg |
| 13 | DOGS:DNAenv complex | IM | 1 | 1 µg | 1 µg |
| 14 | DOGS:DNAenv complex | IM | 2 | 1 µg | 2 µg |
| 15 | DOGS:DNAenv complex | IM | 3 | 1 µg | 3 µg |
| 16 | DOGS:DNAenv complex | NA | 1 | 10 µg | 10 µg |
| 17 | DOGS:DNAenv complex | NA | 2 | 10 µg | 20 µg |
| 18 | DOGS:DNAenv complex | NA | 3 | 10 µg | 30 µg |
| 19 | DOGS:DNAenv complex | NA | 1 | 1 µg | 1 µg |
| 20 | DOGS:DNAenv complex | NA | 2 | 1 µg | 2 µg |
| 21 | DOGS:DNAenv complex | NA | 3 | 1 µg | 3 µg |
| 22 | Naked control DNA | IM | 3 | 100 µg | 300 µg |
| 23 | DOGS:control DNA complex | IM | 3 | 10 µg | 30 µg |
| 24 | DOGS:control DNA complex | NA | 3 | 10 µg | 30 µg |
| 25 | None | — | 0 | 0 | 0 |

IM = intramuscular in divided doses (100 µl) between the hamstring muscles bilaterally.
NA = nasal aerosol administered in small aliquots to 100 µl final volume.
Naked DNA refers to pHenv-DNA in water.
Dioctadecylamidoglyclsperimine (DOGS) was obtained from Promega Corporation (Transfectam ® IBF-Sepracor, France) and complexed to DNA at a 5:1 molar cationic charge excess according to the manufacturer's directions.
Complexes were prepared and used immediately prior to immunization.
pACYC177 DNA was used as an irrelevant control DNA.

TABLE 4

Serum antibody anti-HIVenv responses to DNA immunization.
Serum titers of antibodies against the env proteins of HIV-1 were quantitated with a dot-blot procedure. H9 cells infected with HIV-1$_{IIIB}$ were lysed with RIPA buffer at $10^6$ cells/100 ml and debris removed by centrifugation. One hundred ml of 1:100 dilution in Tris saline of the RIPA lysate were absorbed on a nitrocellulose membrane and the excess sites blocked with bovine serum albumin. Serial dilutions of mouse serum were incubated with each dot blot, washed x3 with TE buffer. Specific IgG, IgM, and IgA titers were determined with excess immunoglobulin class anti-mouse antibodies conjugated with alkaline phosphatase and developed with p-nitrophenylphosphate (PNPP, Pierce Chemical Company) and quantitated in 96-well plate Flow colorimeter using a 414 nm band pass filter. Titer cut-offs are reported as the highest dilution yielding a mean optical density ± 1 S.D. over control.

| | | Number of Immunizations | | | | | |
|---|---|---|---|---|---|---|---|
| | | 1 | | 2 | | 3 | |
| Immunogen (Route) | | % Seroconversion | AV reciprocal titer | % Seroconversion | AV reciprocal titer | % Seroconversion | AV reciprocal titer |
| Naked DNAenv (Intramuscular) | 100 mg | 40 | 25 | 60 | 25 | 60 | 425 |
| | 10 mg | 40 | 25 | 40 | 25 | 40 | 1575 |
| | 1 mg | 0 | 0 | 0 | 0 | 0 | 0 |

TABLE 4-continued

Serum antibody anti-HIVenv responses to DNA immunization.
Serum titers of antibodies against the env proteins of HIV-1 were quantitated with a dot-blot procedure. H9 cells infected with HIV-1$_{IIIB}$ were lysed with RIPA buffer at $10^6$ cells/100 ml and debris removed by centrifugation. One hundred ml of 1:100 dilution in Tris saline of the RIPA lysate were absorbed on a nitrocellulose membrane and the excess sites blocked with bovine serum albumin. Serial dilutions of mouse serum were incubated with each dot blot, washed x3 with TE buffer. Specific IgG, IgM, and IgA titers were determined with excess immunoglobulin class anti-mouse antibodies conjugated with alkaline phosphatase and developed with p-nitrophenylphosphate (PNPP, Pierce Chemical Company) and quantitated in 96-well plate Flow colorimeter using a 414 nm band pass filter. Titer cut-offs are reported as the highest dilution yielding a mean optical density ± 1 S.D. over control.

| | | Number of Immunizations | | | | | |
|---|---|---|---|---|---|---|---|
| | | 1 | | 2 | | 3 | |
| Immunogen (Route) | | % Seroconversion | AV reciprocal titer | % Seroconversion | AV reciprocal titer | % Seroconversion | AV reciprocal titer |
| DOGS/DNAenv (Intramuscular) | 10 mg | 60 | 85 | 67[a] | 315 | 80 | 20 |
| | 1 mg | 80 | 20 | 80 | 40 | 80 | 1750 |
| DOGS/DNAenv (Nasal aerosol) | 10 mg | 20 | 25 | 20 | 125 | 40 | 75 |
| | 1 mg | 40 | >3125 | 40 | >3125 | 80 | 850 |

[a]Two samples not determined.

The Western blot immunoreactivity in seroconverted animals was determined. Western blots were prepared by SDS-PAGE of HIV-1$_{IIIB}$ infected H9 cell lysates with transfer to nitrocellulose achieved with a four-day passive diffusion transfer. Albumin blocked strips were prepared from nitrocellulose sheets and incubated 1 hour with 200 µl of a 1:40 dilution of mouse serum. Detection was achieved with an alkaline phosphatase conjugated anti-mouse antibody and developed with 5-bromo-4-chloro-3'-indolyphosphate p-toluidine/nitro-blue tetrazolium chloride (BCIP/NBT, Pierce Chemical Company). HIVIG obtained from Fred Prince at the New York Blood Center was used as a human positive control. Mouse antisera generated against the terminal twelve amino acids of gp120 was used as a mouse positive control. This antiserum was produced by F-MOC peptide solid phase synthesis, purification of the peptide by HPLC on a C18 column using a TFA/H$_2$O gradient, conjugation to KLH, and administration to mice by multiple intradermal injections using Freund's adjuvant. The major reactivity occurs with gp120 with additional reactivity observed against gp160. No gp41 band was detected by the HIVIG control. Both gp160 and gp120 are equally stained by an anti-human IgG. In this blot preparation no gp41 is observed although gp41 is routinely detect in most of our Western blot preparations. Similar reactivity for IgG is observed against gp160 using an anti-mouse anti-IgG antibody for detection. IgM antibodies were also observed against gp160 although the quantity was diminished compared to the IgG and IgA responses. The lack of apparent gp41 response by genetically immunized mice is likely an artifact of the Western blot preparation since gp41 banding is usually detected by our lab using HIVIG. The clear presence of gp120 bands with both controls suggests that the major reactivity is actually gp41 which is detected on gp160. Alternatively, it may be tetramers of gp41 that are being detecting which are known to run in the gp160 band (181).

Nevertheless, there is a clear, anti HIVenv systemic response to mucosal genetic immunization.

An IgA-specific alkaline phosphatase decoration of lung tissue in an animal immunized with a nasal aerosol of DOGS/HIVenv-DNA was observed. Control animals consistently revealed no labeling of IgA on mucosal surfaces. An anti-HIVenv reactivity of a bronchiolar epithelium in a lung from a mouse immunized by the nasal aerosol delivery of DOGS/HIVenv-DNA was demonstrated. Control animals demonstrated no bronchiolar reactivity towards HIVenv antigens. A fluorescent antibody decoration of colonic mucosa from an immunization via nasal aerosol was observed. This visualization of IgA responses following genetic mucosal immunization and the binding of HIV envelope proteins from H9/IIIB infected cells represents a specific secretory IgA response to mucosal genetic immunization.

Recently obtained Balb/c target cells from Dr. Sunil Chada (182) are being expanding for the detection of CTLs. Although there is extensive experience with the measurement of human neutralization and enhancing antibodies, initial efforts with Balb/c mouse serum revealed an HIV inhibitory factor which has been inactivated with heat at 56° C. for ½ hour. Further neutralization assays using heat inactivated serum will be rigorously standardized using heat inactivated Balb/c serum from mice immunized with HIV-$1_{IIIB}$ as a positive control. This reagent is not available commercially to our knowledge and we are currently immunizing mice with inactivated HIV-$1_{IIIB}$.

Histochemical staining activities in mice immunized with DOGS/HIVenv DNA nasal aerosol was performed. Five-micron frozen sections were prepared from snap frozen (liquid nitrogen) lung and colon of nasal aerosol immunized mice using a refrigerated microtome and adhered to standard silinized glass slides. To demonstrate mucosal antibodies specific for HIVenv determinants, each section was incubated for 30 min to a 1:100 dilution of H9/IIIB cell lysate. The sections were extensively washed with TE buffer and incubated with 100 μl of a 1:100 dilution of HIVIG. Binding of human Ig was detected after extensive washing in TE buffer with a goat anti-human IgG antiserum conjugated with alkaline phosphatase and developed with BCIP/NBT detection of mouse anti-HIV mucosal antibodies in lung sections and goat anti-human IgG antiserum conjugated with fluorescein for detection of anti-HIV mucosal antibodies in colon. Mucosal IgA antibodies were visualized in lung frozen sections using a goat anti-mouse IgA coupled with alkaline phosphatase.

The binding of DOGS to DNA has been studied by molecular modeling using the DREIDING II force field in a Biograf software package (Molecular Simulations, Inc.) on a Silicon Graphics RISC-based computer. After molecular dynamics the molecule is seen to bind to the major groove of DNA. Two of the four positive charges on the polar end of DOGS plus the peptide amide hydrogen symmetrically coordinate with a single phosphate on DNA. One hydrophobic arm extends from the phosphate while the second extends in the opposite direction along the major groove for several methylene groups then bends toward the first arm. This conformation places sequence of 4–5 methylene groups exposed to solvent per phosphate. One of the DOGS lipophilic chains extends into solvent. With a molar charge ratio of 5:1::DOGS/DNA, all phosphate groups will be ionically complexed with a hydrophobic shell covering the entire DNA molecule. This explains the stability of the complex and its affinity for the lipid plasma membrane. It is possible that a structure of this type could survive passage through the acidic environment of the stomach if the DOGS/DNA charge complex is relatively inaccessible to hydrogen ions.

2. Current Status of Bolistic Immunization

Our department has recently obtained the latest version of the "gene gun" from Agricetus (i.e., Accel® Pulse Gun). This is a "12-shooter" in which, DNA bound to 0.95 μm gold particles is physically propelled through plasma membranes using a helium propellant. DNA is bound, to gold, evenly dispersed and dried in ⅛" OD polyethylene tubing, and cut to standard ½" lengths. An initial study to determine the optimal helium pressures for skin penetration to basal layer and Langerhans cells in dorsal and vertical skin of 5 week and 6 months old Balb/c mice has been completed. Sections are processed to histologically determine the level of gold penetration and to determine by immunohistochemistry whether expression of the HIVenv proteins on the plasma membrane of keratinocytes or Langerhans cells can be detected.

3. Vector Design and Synthesis

Figure 2:
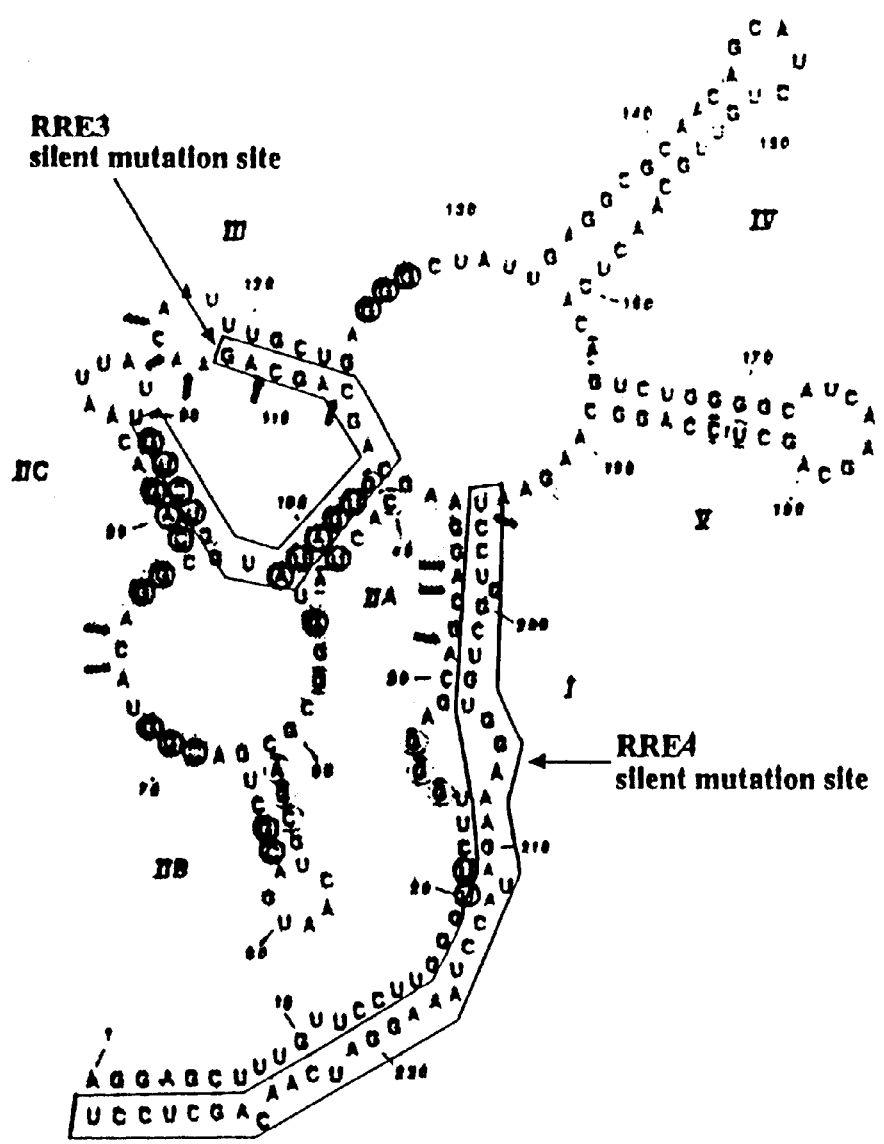
FIG. 2 is a diagram of the RRE of HIV-1$_{NL4-3}$ and the sites of mutagenesis designed to yield silent mutations.

The vector used for our pilot genetic immunization study, pHenv, is a 9600 bp plasmid containing SV40 promoters. The HIV envelope sequences, however, are contained within LTRs with fully functional tat and rev genes plus the RNA receptor sites TAR and RRE, respectively. Presumably, the expression of gp160 is under LTR promoter control. A central feature in our proposal is to examine whether this expression system is the most advantageous for expressing the env proteins and for inducing functional immune responses. Not only gp160 but gp120 and gp41 wil be expressed separately or in combination. One possible problem is the extensive secondary structure of the RRE which has caused us difficulties in our initial site-directed mutagenesis efforts on the primary enhancing domain of gp41. We have, therefore, introduced silent mutations (i.e., no alteration in amino acid sequence of gp41) designed to abolish the secondary structure of the RRE. We have produced two such mutations. RRE-3C is designed to disrupt the binding site for Rev while RRE-4C will more extensively disrupt the entire RRE. FIG. 2 illustrates the RRE and the mutagenized sites. pHenv was cut with SalI and EcoRI and the 4700 bp gp160 sequence isolated from agarose following electrophoresis. This sequence was cloned into the pAlter MCS, subjected to site-directed mutagenesis, on the RRE, ampicillin (repair), and tetracycline (sensitivity) sites and selected with ampicillin. Mutagenized RRE yield the correct size and restriction sites following antibiotic selection. Sequence analysis is being performed to confirm that a silent mutation of the RRE have been constructed.

Our pilot genetic immunization studies used an, irrelevant plasmid as a control DNA. Although adequate, a better control would be pHenv lacking all HIV sequences. A recircularized pHenv without the HIV insert and containing a new SnaB restriction site has been constructed. This plasmid can be the control DNA for all future genetic immunizations using pHenv.

4. Molecular Modeling of the HIV Envelope Proteins

Although the primary sequence of the HIV env-proteins are hypervariable, certain structural features remain constant among all isolates. FIG. 2 is a representation of the structural data for gp120 reported by Leonard et al. (174) in which disulfide pairings were identified by classical chemical methods and generic glycosylation patterns (sialated vs non-sialated) were assigned by enzymatic methods. Included in FIG. 2 is the single disulfide present in gp41 and its N-linked, glycosylation sites of unknown structures. These structural relationships are combined with the neutralizing and enhancing antibody binding domains reviewed by Robinson and Mitchell (178). There are nine disulfide bonds and one free sulfhydryl in gp120. The positions of the cysteine residues in gp120 is highly conserved in all isolates with the exception of the Z3 isolate in which an additional two cysteines are present in the fourth hypervariable domain. This strongly suggests that the disulfide pairing in $III_B$ is maintained among all isolates. Using the Dreiding II generic force field for molecular simulations, Gabriel and Mitchell (172) have generated molecular simulations for a truncated gp120 which agree with all known, data concerning gp120 glycosylation, antigenic structure and gp120/CD4 binding interactions. Docking inhibition studies with known gp120/CD4 binding inhibitors have recently been completed that provides further credence to our model (179). Similar modeling studies with gp41 in which the Cys-Cys loop of gp41 has been docked to the C-terminal concavity on gp120 in agreement with the theoretical predictions of Moore et al. (149) have been conducted. There is a model for the relationships between the major antigenic sites on gp120 and N-linked oligosaccharides gp120 is docked to CD4. The V3 loop is solvent accessible on one face although a portion is obscured by carbohydrate. The second conserved domain is accessible from one side only. The CD4-binding domain is completely obscured by carbohydrate on one face but is easily accessible on the opposite face. The present ability to provide a model structure in which the effects of sequence variation in our genetic immunogens can be predicted is a valuable tool that will aid us in their design and analysis of those biological responses that are dependent on structural changes in the protein immunogen.

5. Rationale and Significance to the National HIV Vaccine Program

We have been able to generate specific anti-HIVenv responses in Balb/c mice by facilitated genetic immunization of mucosa. Mice are currently being, immunizing against HIV-$1_{IIIB}$ in order to obtain a mouse polyclonal control HIV neutralizing serum obtained by conventional methods. We have extensive experience in the quantitation of functional humoral responses towards HIV in humans and anticipate no difficulty despite our surprise with the natural anti-HIV activity of mouse serum we initially obtained. Since genetic immunization has been shown to generated CTL responses, we have obtained during the past two weeks from Dr. Sunil Chada of Viagene Inc. in San Diego two unique cell lines that will enable us to evaluate cytotoxic lymphocyte (CTL) responses in Balb/c mice as a function of immunization (182). The Hu/$D^d$ line is a CD4 expressing HeLa derivative that carries and expresses the $D^d$ MHC locus of the Balb/c mouse. This line can be infected with a wide variety of established and primary HIV isolates to be used as a target for Balb/c CTLs. The second is a Balb/c fibroblast that has been permanently transfected with HIVenv (IIIB) sequences which are expressed on the cell surface. This cell provides another suitable target for CTL analysis in Balb/c mice as a function of immunization against HIV. The second observation is from the laboratory of Dayne at the University of Utah. He has reproducibly been able to convert systemic immune responses from conventional protein immunization to mucosal type responses by the inclusion of nanogram quantities of 1,25 (OH)$_2$D3 in his vaccine preparations (2). We have recently obtained a large supply (5 mg) of this active Vitamin D3 from Hoffman-LaRoche. We have also recently obtained access to an Agricetus gene gun which will allow us to extend and evaluate Dr. Dayne's original observation to epidermal genetic immunization. We will be able to directly compare both methods for the production of functional mucosal responses against HIV with each vector formation that we produce.

Although beyond the immediate scope of this application is the production of DNA immunogens that lack the capacity to induce C'-ADE responses. We are currently evaluating gp160 mutations that we have constructed for this capacity. We envision the fusion of both avenues of research (i.e., planned and current) to a final product for consideration as a HIV vaccine candidate.

Lastly, genetic immunization allows the construction. of a product in which the genetic variability observed for HIV can be multiply mimicked in a single product for those regions of importance.(i.e., V3 loop). Genetic immunization is the only practical way in which this hypervariability of the pathogen can be reproduced.

4. Method Design and Protocols

A. General Design

Our initial evaluation will use pHenv as the common vector in the direct comparison of mucosal and systemic responses to genetic immunization. Balb/c mice in two age groups (6 weeks and 6 months) will be evaluated for serum titers of Igs, Western blot and radioimmunoassay specificities of immune humoral responses, sIgA titers in parotid secretions, direct visualization of mucosal antibodies specific for HIV, neutralizing titer of serum and parotid antibodies, and spleen CTL activity against $^{51}$Cr labeled against target BCenv and Hu/$D^d$/HIV. The ability of DOGS/DNAenv complexes to induce a common mucosal response will be evaluated with nasal aerosols, colonic exposure, vaginal exposure, and gastric delivered formulations. In each case we will do dose response analysis using 10 µg DNA as our highest total DNA single dose exposure. We will similarly evaluate responses as a function of one, two, or three genetic immunization schedules allowing 2 week and/or 3 month intervals between responses. We plan to similarly evaluate bolistic immunization of mouse skin with and without 1,25(OH)$_2$D3 supplementation. After we establish the optimal helium delivery pressure for each age of mice and have established a dose response for site injected 1,25(OH)$_2$D3, we will evaluate the inclusion of the vitamin in the bolistic DNA/Au formulations in order to establish whether a single formulation is possible. If feasible, we will further establish stability of the formulation under various physical conditions.

While we are evaluating the various routes and modes of genetic immunization outlined above, we will develop a variety of DNA constructs that may have major impact on the quality and quantity of immune responses to genetic mucosal immunization. We plan to examine the effect of various eukaryote promoters on immunogen expression. The most effective eukaryotic promoter examined to date for genetic immunization is the CMV promoter for HBV subunit expression (18) although the field has not been systematically examined. We will examine the thymidine kinase promoter for herpes simplex virus (HSV) using pTKb (GenBank accession # U02438), the SV40 early promoter using pSVb (GenBank accession # U02435), the CMV immediate early gene promoter using pCMV-Lic (Contains CMV promoter/enhancer LIC cloning site, HGH polyadenylation site, and SV40 early promoter) or pCMVb (GenBank accession # U02451), and the adenovirus major late promoter (GenBank accession # U02442). Using gp160 lacking the LTRs we plan to evaluate which vector provides maximal expression in a variety of eukaryote cell lines, such as HeLa and SG181 (a human fibroblast) and human H9 as well as primary mouse lung, intestinal, and skin explant organ cultures. Those promoters providing the best consistent expression will be used in our subsequent vector constructs.

Following identification of the best promoter(s) for surface expression in target eukaryote cells, we will prepare vector constructs which are designed to identify the best signal peptide sequences (i.e., the HIV signal sequence vs TPA signal peptide for example), expression from a vector carrying the RRE secondary structure vs silent mutations in which the RRE secondary structure has been eliminated without alterations to the primary amino acid sequence, gp160 vs gp120 and/or gp41 containing the gp160 membrane anchor domain, and gp160 in which the gp160 cleavage site has been eliminated. Following identification of the best constructs for genetic immunization we plan to also construct a vector with HIVenv sequences plus p17 since an N-terminal neutralization site has been identified in this HIV gag protein. The bottom line is that we will search for the best plasmid vector construct that can be identified in order to maximize both the quality and quantity following genetic immunization.

Genetic immunization offers the best opportunity for generating multiple responses to the various hypervariable forms of the Principle Neutralizing Domain of HIV (i.e., V3 loop). We will generate V3 loop mutations on a pNL4-3 DNA envelope sequence that reflect the major macrophagetrophic and lymphotrophic variants of clade B viruses as well as those limited V3 loop sequences recognized by the Ho laboratory (171) to be the infectious variant from a multiplicity of potential infectious variants of the infecting donor. For each V3 loop variant we will examine the effect on gp120/gp41 conformation by molecular modeling in order to anticipate alterations on group-specific conformational epitopes. Lastly, we will examine the response to DNAenv cocktails containing multiple V3 loop species.

Detailed Protocols

1) Facilitated DNAenv mucosal immunization

Dioctadecylamidoglycylspermine (DOGS) obtained from Promega as Transfectam® will be solubilized in 100% ethanol and complexed to DNA in $H_2O$ at a 5:1 molar cationic charge excess and diluted in Tris-saline to the immunization dose based on DNA concentration and administered immediately following formulation. One hundred $\mu l$ will be administered as a nasal aerosol, gastric bolus, or colonic bath or 25 $\mu l$ deposited intravaginally to anesthetized (ketamine/xylazine) female Balb/c mice of six weeks or six months age. All animals will be randomized into groups of five. Each animal will be euthanized by exsanguination under ketamine/xylazine anesthesia three weeks after the final immunization. Whole blood will be collected by abdominal aorta catherization (#25 pediatric cut-down set). The spleen will be collected and teased for white pulp and PBMCs isolated on Hypaque-Ficol. Lungs, colon, small intestine, and vagina will be collected and snap frozen in liquid nitrogen for subsequent frozen section processing.

2) Vector Constructs a. HIVenv DNA cloning using LIC-based PCR: Ligation-independent cloning is based on the methods of Aslanidis and dejong (183) and Haun et al. (184). Sense (5'-CTGGTTCCGGCGA[gene specific primer]-3') and anti-sense (5'-CTCGCTCCGGCGA[gene specific primer]-3') primers will be prepared by standard oligonucleotide synthesis and purification procedures or obtained from IDT Corp. (Coraville, Iowa). PCR amplification using Vent® DNA polymerase uses hybridization and extension times and temperatures theoretically calculated with Intelligenetics® software 5'-overhangs are generated from the dsDNA product by digestion with T4 polymerase in the presence of dTTP which terminates digestion from each 3'-end at the first thymidine. A 10 molar excess of 5'-overhang DNA is hybridized with 25 mg LIC vector DNA at room temperature for ½ hour. The hybridized product is used in a standard transformation protocol on competent HB101 or JM109 E. coli cells and selected on ampicillin plates. We have produced a variety of PCR LIC inserts of, HIV regulatory, accessory, and envelope genes by this method. In addition we have been able to introduce new unique restriction sites on either end of the cloned gene, start or stop codons by the insertion of sequences between the LIC hybridization sequence and the gene specific. hybridization site. This is a powerful method for directional cloning and the introduction of limited new sites external to the gene-specific site.

b. Site-directed mutagenesis: We routinely use the p-Alter® method for the introduction of mutations at specific sites. A SalI/EchoRI agarose purified restriction fragment of pHenv containing the $HIV_{NL4-3}$ envelope sequence was cloned into the p-Alter vector. This vector contains a mutant ampicillin resistance gene and a tetracycline resistance gene for selection during multiple rounds of additive mutagenesis. JM109 E. coli transformed with p-$Alter_{HIVenv}$ are induced to produce single strand (ss) DNA using helper phage DNA. Three mutational primers are hybridized at room temperature to the ssDNA (ampicillin resistance repair primer, tetracyline resistance inactivation primer, and a mutational primer of the gene under analysis). The hybridized DNA is filled in with T7 polymerase and mutant repair E. coli used for transformation and mutagenized plasmid recovery on antibiotic selection plates. This method in our hands has provided us the highest yield of desired sequence verified mutations of the various methods we have tested. The critical factors concern the purity of phage DNA and the use of MutS-Blue E. coli lacking all DNA repair systems.

3) Bolistic DNA Immunization

Fifty $\mu g$ (0.95 $\mu m$) gold beads are mixed with 100 $\mu l$ 0.1 M spermidine in a 1.5 ml microfuge tube, sonicated 5 seconds, and an equivolume or less of plasmid DNA at a concentration yielding 0.1–5.0 $\mu g$ DNA/mg gold is added and mixed by vortex. 200 $\mu l$ 2.5 M $CaCl_2$ is added during vortexing, and the mixture allowed to precipitate at room temperature for 10 minutes. The mixture is briefly centrifuged to precipitate any remaining gold in solution. The supernatant is discarded. The pellet is washed x3 with 500 $\mu l$ ethanol at 4° C. with a 30 second microfuge spin between washes. The ethanol volume is adjusted to 7 mg gold/ml, vortexed, and sonicated (3 sec), and 500 $\mu l$ transferred to rotating ⅛" OD Tefzel polyethylene tubes fitted horizontally in an Agricteus tube turner. The beads are allowed to settle (5 minutes). Mechanically excess ethanol is slowly removed and rotation begun at 20 rpm. After 30 sec the tube is dried with $N_2$ at 0.4 lpm. The tube is then cut into ½" sections. For quality control each end of the tubing is assayed by light microscopy for gold bead number and penetration at the desired psi into 3% agar. Tubes are stored at 4° C. in a desiccant.

Mouse skin is prepared for bolistic transfection by initial shearing with an Oster fine shear clipper and finally prepared with a Panasonic dry/wet electric shaver. The ½ inch tubes with adherent DNA complexed to gold are loaded into the Accel® Pulse Gun and the DNA/gold complex propelled by He at a predetermined psi for optimal penetration of skin based on species, site, animal age, and distance from skin (standard). The site of penetration is easily observed and can be indelibly marked with India ink for subsequent processing as required.

4) Systemic Antibody Analysis a. Ig Titers. Serum titers of antibodies against the env proteins of HIV-1 are quantitated with a dot-blot procedure.

H9 cells infected with HIV-$1_{IIIB}$ are lysed with RIPA lysis buffer (0.05 M Tris-HCl, pH 7.2, 0.15 M NaCl, 0.1% SDS, 1% Triton X-100, 1% deoxycholate, 1 mM phenyl methyl sulfonyl fluoride) at $10^6$ cells/100 µl and debris removed by centrifugation. One hundred µl of 1:100 dilution in Tris saline of the RIPA lysate are absorbed on a nitrocellulose membrane and the excess sites blocked with bovine serum albumin. Serial dilutions of mouse serum are incubated with each dot blot, washed x3 with TE buffer. Total Ig or specific IgG, IgM, and IgA titers are determined with excess anti-mouse Ig antibody immunoglobulin class anti-mouse antibodies conjugated with alkaline phosphatase and developed with p-nitrophenylphosphate (PNPP, Pierce Chemical Company) and quantitated in 96-well plate Flow colorimeter using a 414 nm band pass filter. Within the next six weeks we should have an optical density scanner that will allow us to perform OD scans directly in dot blots. Titer cut-offs are reported as the highest dilution yielding a mean optical density ±1 S.D. over control.

b. Western blot. Western blots are prepared by SDS-PAGE of HIV-$1_{IIIB}$ infected H9 cell lysates with transfer to nitrocellulose achieved with a four-day passive diffusion transfer. Albumin blocked 'strips are. prepared from nitrocellulose sheets and incubated 1 hour with 200 µof a 1:40 dilution of mouse serum. Detection is achieved with an alkaline phosphatase conjugated anti-mouse antibody and developed with 5-bromo-4-chloro-3'-indolyphosphate p- toluidine/nitroblue tetrazolium chloride (BCIP/NBT, Pierce Chemical Company). HIVIG obtained from Fred Prince at the New York Blood Center is used as a positive control with, an anti-human alkaline phosphatase detection system.

c. Radioimmunoprecipitation analysis (RIPA). H9/IIIB cells are labeled with $^{35}$-cysteine in a cysteine-free medium for 4 hours at 1 mCi/ml containing $1 \times 10^6$ cells. The cells are washed x3 in PBS lysed in RIPA buffer (see 4a above). We attempt to achieve $20 \times 10^6$ cpm with $2 \times 10^5$ cpm/µl. Sera to be tested are incubated with 100 µl of a diluted Protein G-sepharose (Pierce) for 1 hour at 4° C. Lysate is added at an equivalence of 0.5 to $1 \times 10^6$ cells. The serum antibodies and lysate antigens are incubated overnight at 4° C., washed in RIPA wash buffer (i.e., RIPA lysis buffer minus deoxycholate and phenyl methylsulfonyl fluoride). The immune complex-Protein G beads are centrifuged at 1000 g, washed x3 with 4 ml RIPA wash buffer, denatured at 100° C. for 2 minutes and run on SDS-PAGE in 10% resolving gels. After electrophoresis the gel is fixed in 30% methanol, 10% acetic acid, 60 dd$H_2$O or equivalent and radioactive bands visualized with a Molecular Dynamics PhosphoImager.

d. Neutralization Assays.

(i) Standard microtiter neutralization assay. Neutralizing antibody activities will be measured in microtiter infection assays as originally described from this lab (183). Briefly, heat-inactivated (60° C., 30 min.) serum samples will be two-fold serially diluted in triplicate into RPMI 1640 growth medium containing 12%. FCS. Virus will be added (5–10× $10^5$ infectious units) and incubated at 37° C. for one hour. Next, $2-5 \times 10^5$ MT-2 cells in 100 µl of growth media will be added to each well and the plates incubated for 2–3 days at 37° C. in 5% $CO_2$/95% air. Cells will be monitored by phase contrast microscopy for syncytia formation and assayed when virus control wells (no mouse serum) show extensive cytopathic effect. This usually is at 3 ½ days when MOI$\geq$1 is used. Cells are transferred to poly-L-lysine coated plates and incubated with Finter's neutral red dye for 1 hr. Adherent cells are washed with phosphate-buffered saline (PBS) and vital dye liberated with acid alcohol. Plates will be analyzed on a Flow Titertek microcolorimeter at 540 nm for viable cells. Viability will be determined relative to the cell control wells (n=4). Neutralizing titer is defined as the highest dilution yielding $\geq$50% cell viability compared to cell control.

(ii) Primary isolate neutralization. The gold, standard for neutralization is the ability to neutralize the ability of a panel of primary isolates to infect human PBMC. The latter are freshly isolated on Hypaque-Ficol. $5 \times 10^6$ cells in 10 µl of undiluted primary isolate HIV (i.e., always propagated on PBMCs) are incubated in triplicate in serial 5 fold dilutions of mouse serum for 1 hour at 4° C. and then added to 1 ml RPMI/12% FCS containing biological derived IL2. Supernatants at 7 days are assayed for RT and/or p24 levels versus control cultures. The highest dilution to yield 24 50% inhibition is reported as the neutralization titer.

5) Mucosal Antibody Analysis a. Parotid secretion IgA/IgG titers: Titers will be monitored weekly for short term immunization schedules and monthly on long term schedules. Parotid secretion in anesthetized (IM ketamine/xylazine) Balb/c mice will be induced with pilocarpine (20 µg/mouse) and saliva collected on specified days with a Pasteur pipette. Analysis of 2 fold serial dilutions will be determined by a dot blot procedure described under 4 a above. Detection of specific responses to various V3 loop expression immunogens, parotid secretions will be titered using V3 loop peptides synthesized on our Miligen 9050 peptide synthesizer by the F-moc method. One µg of synthetic. peptide in 100 µl of coating buffer (0.1 M bicarbonate buffer [pH9.6]) are added to each well of Immulon 2 microtiter plates and incubated at 37° C. for 2 h. The wells are next washed three times, in phosphate-buffered saline (PBS) containing 0.05% Tween 20, and then serially diluted (2 fold) saliva is added to each of triplicate wells. After incubation for 2 h at 37° C., the wells were washed three times with washing buffer. Next, goat anti-mouse immunoglobulin A or G (heavy- and light-chain specific) coupled to horseradish peroxidase is added at a dilution of 1:1,000 and incubated for another hour at 37° C. After the wells are washed five times with PBS containing 0.05% Tween 20, 2,2'-azino-bis(3-ethylbenzthiazoline sulfonate) (ABTS) is added as the substrate and incubated for 30 min at room temperature. The optical density (OD) of each well is read in an enzyme-linked immunosorbent assay (ELISA) reader at 410 nm. For more detailed descriptions of our procedures and analysis please refer to Refs 143–145.

b. Immunocytochemistry: Five-micron frozen sections are prepared from snap frozen (liquid nitrogen) lung, colon, jejunal and vaginal tissues of genetically immunized mice using a refrigerated microtome and adhered to standard silinized glass slides. To demonstrate mucosal antibodies specific for HIVenv determinants, each section is incubated for 30 min in a 1:100 dilution of H9/IIIB cell lysate (1:100::RIPA:Tris saline). The sections are extensively washed with TE buffer and incubated with 100 µl of a 1:100 dilution of HIVIG. Binding of human Ig (HIVIG) is detected after extensive washing in TE buffer with a goat anti-human IgG antiserum conjugated with alkaline phosphatase and developed with BCIP/NBT detection of mouse anti-HIV mucosal antibodies in lung and vaginal sections and goat anti-human IgG antiserum conjugated with fluorescein for detection of anti-HIV mucosal antibodies in jejunum and colon. Mucosal IgA and IgG antibodies are visualized in frozen sections using a goat anti-mouse IgA coupled with alkaline phosphatase or fluorescein.

6) Analysis of Cytotoxic Lympocyte Activity against HIV Expressing Targets (CTLenv)

CTLenv will be quantitated using the H/D$d$ cell line infected with primary HIV isolates, or the murine BCenv.

line (HIV expressing) as described earlier under Preliminary Data. Uninfected Hu/$D^d$ and BCgal (b galactosidase expressing) will be used as controls, respectively. Target cells will be intracellularly loaded with $^{51}$Cr by incubation for 45 min under 5% $CO_2$ 1.5×10$^6$ cells in RPMI 1640 with 150 μl $Na_2^{51}CrO_4$ in PBS (1 mCi/ml, specific activity 400–1200 ° Ci of Cr per gram from DuPont/NEN). Labeled cells are washed in cold RPMI/10% FCS ×3 and kept on ice for cytotoxicity assay. Mouse spleen mononuclear cells isolated by Hypaque-Ficol are added to target cells (10$^4$ cells in 100 μl RPMI 1640/10% FCS) at effector:target ratios of 100:1, 50:1, 25:1, and 12.5:1, incubated at 37° C. under 5% $CO_2$ for 4 hours, centrifuged, and 100 μl counted in a Gamma counter. Control target cells are lysed with 5% Triton X-100 to obtain maximal release values and cytotoxicity calculated by % cytotoxicity =\|f( exptl release—spontaneous, release, maximal release 'spontaneous release )×100.

7) Analysis of the Persistence of Transfected DNAenv in Tissues

Primary transfection site tissues will be harvested as a function of time following transfection and aliquots lysed in 1% Triton X-100, 10 mM Tris, pH 7.0, and 1 mM EDTA, centrifuged at 1000×g to remove insoluble debris, and the supernatant removed and heated to 100° C. for 5 minutes. Analysis for DNAenv will use PCR amplification of the V3–V5 regions using ED5 (5'-ATGGGATCAAAGCCT AAAGCCA TGTG) and ED12 (5'-AGTGCTTCCTGC TGCTCCCAAGAACCCAAG) primers which yields a 1200 bp DNA product corresponding to ~bp 6160–7358. Standard conditions for this gene product in a 50 μl volume is 35 cycles with 1 second ramp times between steps of 94° C. for 60 s, 55° C. for 60 s and 72° C. for 120 s with cycling initiated following a 5-min incubation at 95° C. and wax bead "hot start." The PCR reaction used 0.2 μM of each primer in 50 mM KCl, 10 mM Tris-HCl (pH 8.3), 200 μM of each dNTP, 2.5 U Taq DNA polymerase and 1.5 mM MgCl. Two to ten μl of the cell lysate is used as template. Amplified DNA is separated and identified by electrophoresis in 1.2% agarose or 6% polyacrylamide gels run in TBE buffer (88 mM Tris-borate, 89 mM boric acid, 2 mM EDTA) at 120 volts for 1 hr. DNA bands are identified by ethidium bromide staining and UV light detection. Primer specificity is verified by using pNL4-3 plasmid derived DNA and total genomic obtained from ACH-2 cells (positive control).

8) In situ Analysis of DNAenv Transfected Cell Types

In situ hybridization of a PCR amplified DNA using suitable probe of high specificity will allow the detection of transfected DNAenv in a normal cellular architecture that would otherwise be undetectable. Biopsy specimens from the transfected tissues are fixed for 1 hour in a non-crosslinking, water soluble fixative [Strekk Tissue Fixative (STF)], embedded in paraffin tissue blocks, sections mounted on polylysine coated glass slides and processed for routine H&E histology. In order to perform PCR amplification, 4 μm sections containing three sections per slide are deparaffinised by successive washes in xylene and progressively diluted alcohol solutions. Deparaffinised slides are subjected to proteinase K permeabilization of the plasma membranes (10 μg/ml for 20 min at RT). Each membrane permeabilized slide is then placed on the hot stage (5°> primer melt temperatures) of the Perkin-Elmer In Situ PCR slide Prep apparatus. Two sections serve as controls (i.e., one lacking primers as, negative control and a second using a housekeeping gene amplification such as F-actin as positive control for. membrane permeabilization).

Thirty-five μl of PCR mix containing the appropriate ions and pH found optimal for solution PCR (i.e., $MgCl_2$, KCl, in 10 mM Tris-HCl) and 7.5 units of Ampli-Taq DNA polymerase) plus the primers described above for'solution PCR but containing a 5'-biotin (prepared on our DNA Cyclone) plus primers for the housekeeping control. Each section is sealed with a disposable plastic chamber and external metal clamp that serves as a heat sink. Each prepared slide is transferred in succession to the In Situ PCR Cycler held at the temperature Slide Prep apparatus and which has a capacity of ten slides. Temperature cycling times are those previously established using solution PCR. This procedure provides a hot start to minimize non-specific primer binding and polymerase extension during the procedure set-up. Following in situ amplification of specific, DNA sequences, detection is provided by strepavidin conjugated to alkaline phosphatase to detect specific sequences of the amplified DNA containing 5'-biotin. The water soluble substrate (nitrobluetetrazolium and 5-bromo-4chloro-3'-indoylphosphate p toluidine) is precipitated at the site, of enzyme catalyzed substrate hydrolysis forming a blue stain of transfected cells. This is new technology that requires the Perkin-Elmer In Situ PCR equipment for optimal performance. We currently have this equipment on order with promised delivery in the immediate future. We have solution PCR experience as well as limited in situ PCR experience with human PBMCs. We anticipate little difficulty in adapting to this state-of-the-art methodology and equipment.

9) Toxicity of in vivo Transfecting DNA

Although the facilitated DNA and bolisitc DNA transfection methods use small amounts of DNA and the cells transfected are in regenerating tissues with continual sloughing in contrast to the large amounts of DNA required for genetic immunization of muscle tissue, the FDA will undoubtedly require toxicity testing of the plasmid vectors for acute and chronic toxicity prior to approving any Phase I clinical trial of a candidate DNA immunogen. The most likely chronic toxicity is the development of antibodies to DNA. We will monitor mice, rats, guinea pigs, and rabbits for the development of antibodies to plasmid vector DNA using an ELISA format in which DNA is adhered to Immunolon plates as previously described for peptide antigens and albumin blocked wells exposed to serum from transfected animals. Antibodies binding to DNA will be detected by anti-mouse (or rat, guinea pig, or rabbit) Ig conjugated to alkaline phosphatase. Quantitation will be based on enzyme yields minus control animal enzyme yields under conditions of substrate excess (i.e., to yield zero order kinetics).

Throughout this application various publications are referenced by numbers within parentheses. Full citations for these publications are as follows. The disclosures of these publications in their entireties are hereby incorporated by reference into this application in order to more fully describe the state of the art to which this invention pertains.

Literature Cited

1. Ulmer J B, Donnelly J J, Parker S E, Rhodes G H, Felgner P L, Dwarki V J, Gromkowski S H, Deck R R, DeWitt C M, Friedman A, Hawe L A, Leander K R, Martinez D, Perry H C, Shiver J W, Montgomery D L, and Liu M A. Heterologous protection against influenza by injection of DNA encoding a viral protein. *Science* 1993, 259:1745–1749.

2. Dayne R A, and Aranes B A. The development of effective vaccine adjuvants employing natural regulators of T-cell lymphokine production in vivo. Ann NY Acad Sci 1994, 730:144–161.

3. Wolff J A, Malone R W, Williams P, Chong W. Acsadi G, Jani A, and Felgner P L. Direct gene transfer into mouse muscle in vivo. Science 1990, 247:1465–14 1468.
4. Lin H. Parmacek M S, Morle G, Bolling S, and Leiden J M. Expression of recombinant genes in myocardium in vivo after direct injection of DNA. Circulation 1990, 82:2217–2221.
5. Acsadi G, Jiao S, Jani A, Duke D, Williams P, Chong W, and Wolff J A. Direct gene transfer and expression into rat heart in vivo. New Biologist 1991, 3:71–81.
6. Kitsis R N, Buttrick P M, McNally E M, Kaplan M L, and Leinwald L A Hormonal modulation of a gene injected into rat heart in vivo. Proc Natl Acad Sci USA 1991, 88:4138–4142.
7. Hansen E, Fernandes K, Goldspink G, Butterworth P. Umeda P K, and Chang K-C. Strong expression of foreign genes following direct injection into fish muscles. FEBS Lett 1991, 290:73–76.
8. VonHarsdorf R, Schott R J, Shen Y T, Vatner S F, Mahdavi V, and Nadalginard B. Gene injection into canine myocardium as a useful model for studying gene-expression in the heart of large animals. Circ Res 1993, 72:688–695.
9. Gal D, Weir L, LeClerc G, Pickering J G, Hogan J, and Isner J M. Direct myocardial transfection in 2 animals models: evaluation of parameters affecting gene-expression and percutaneous gene delivery. Lab Invest 1993, 68:18–25.
10. Cox G J M, Zamb T J, and Babiuk L A. Bovine herpesvirus 1:immune responses in mice and cattle injected with plasmid DNA. J Virol 1993, 67:5664–5667.
11. Jiao S, Williams P, Berg R K, Hodgeman B A, Liu L, Repetto G, and Wolff J A. Direct gene transfer into nonhuman primate myofibers in vivo. Hum Gene Ther 1992, 3:21–33.
12. Davis H L, Demeneix B A, Quantin B, Coulombe J, and Whalen R G. Plasmid DNA is superior to viral vectors for direct gene transfer into adult mouse skeletal muscle. Hum Gene Ther 1993, 4:733–740.
13. Yankauckas M A, Morrow J E, Parker S E, Abai A, Rhodes G H, Dwarki V J, and Gromkowski S H. Long-term anti-nucleoprotein cellular and humoral immunity is induced by intramuscular injection of plasmid DNA containing NP gene. DNA Cell Biol 1993, 12:771–776.
14. Fynan E F, Robinson H L, and Webster R G. Use of DNA encoding influenza hemagglutinin as an avian influenza vaccine. DNA Cell Biol 1993, 12:785–789.
15. Montgomery D L, Shiver J W, Leander K R, Perry H C, Friedman A, Martinez D, Ulmer J B, Donnelly J J, and liu M A. Heterologous and homologous protection against influenza A by DNA vaccination: optimization of DNA vectors. DNA Cell Biol 1993, 12:777–783.
16. Wang B, Ugen K E, Srikantan V, Agadjanyan M G, Dang K, Refaeli Y, Sato A I, Boyer J, Williams W V, and Weiner D B. Gene inoculation generates immune responses against human immunodeficiency virus type 1. Proc Natl Acad Sci USA 1993, 90:4156–4160.
17. Wang B, Boyer J, Srikantan V, Coney l, Carrano R, Phan C, Merva M, Dang K, Agadjanan M, Gilbert L, Ugen K E, Williams W V, and Weiner D B. DNA inoculation induces neutralizaing immune responses against human immunodeficiency virus type 1 in mice and nonhuman primates. DNA Cell Biol 1993, 12:799–805.
18. Davis H L, Michel M-L, and Whalen R G. DNA-based immunization induces continuous secretion of hepatitis B surface antigen and high levels of circulating antibody. Hum Mol Genet 1993, 2:1847–1851.
19. Davis H L, Whalen R G, and Demeneix B A. Direct gene transfer into skeletal muscle in vivo: factors affecting efficiency of transfer and stability of expression. Hum Gene Ther 1993, 4:151–159.
20. Johnson R P, Hammond S A, Trocha A, Siliciano R F, and Walker B D. Epitope specificity of MHC restricted cytotoxic T lymphocytes induced by candidate HIV-1 vaccine. AIDS Res Hum Retroviruses 1994, 10:573–575.
21. Hui K M, Sabapathy T K, Oei A A, and Chia T F. Generation of allo-reactive cytotoxic T lymphocytes by particle bombardment-mediated gene transfer. J Immunol Methods 1993, 171:147–155.
22. Haynes J R, Fuller D H, Eisenbraun M D, Ford M J, and Pertner T M. Accello particle-mediated DNA immunization elicits humoral, cytotoxic, and protective immune responses. AIDS Res Human Retroviruses 1994, 10:543–545.
23. Eisenbraun M D, Fuller D H, and Haynes J R. Examination of parameters affecting the elicitation of humoral immune responses by particle bombardment-mediated genetic immunization. DNA Cell Biol 1993, 12:791–797.
24. Tang D-C, Devit M, and Johnston S A. Genetic immunization is a simple method for eliciting an immune response. Nature 1992; 356:152–154.
25. O'Hagan D T. Oral immunization and the common mucosal immune system. In Novel Delivery Systems for Oral Vaccines, Derek T. O'Hagan, ed. CRC Press, Cleveland, Ohio, 1994, pp. 1–24.
26. Service R F. Triggering the first line of defense. Science 1994, 265:1522–1524.
27. Suharyona, Simanjuntak C, Witham N, Punjabi N, Heppner D G, Losonsky G. Totosudirjo H, Rifai A R, Clemens J. Lim Y L, Burr D, Wasserman S S, Kaper J, Sorenson K, Cryz S, and Levine M M. Safety and immunogenicity of single-dose oral cholera vaccine CVD 103-HgR in 5–9 year old children. Lancet 1992, 340:689–694.
28. Desrosiers R C. HIV with multiple gene deletions as a live attenuated vaccine for AIDS. AIDS Res Hum Retrovir 1992, 8:411–421.
29. Cohen J. AIDS Vaccines. At conference, hope for success is further attenuated. Science 1994, 266:1154.
30. Padian N S. Heterosexual transmission of acquired immune deficiency syndrome: international perspective and national projections. Rev Infect Dis 1987; 9:947–960.
31. Piot P, Plummer F, Mhalu F S, Lamboray J L, Chin J, and Mann J M. AIDS: an international perspective. Sicence 1988, 239:573–579.
32. Johnson A M. Heterosexual transmission of, human immunodeficiency virus. Brit Med J 1988, 296:1017–1029
33. Hospedales J. Heterosexual spread of HIV infection. Rev Infect Dis 1989, 11:663–665.
34. deSschryver A, and Meheus A. Epidemiology of sexually transmitted diseases: the global picture. Bull WHO 1990, 68:639–654.
35. Alexander N J. Sexual transmission of human immunodeficiency virus: virus entry into the male and female genital tract. Fertil Steril 1990, 54:1–18.
36. Miller C, and Gardner M B. AIDS and mucosal immunity: usefulness of the SIV macaque model of genital mucosal transmission. J AIDS 1991, 4:1169–1172.
37. McGhee J R, and Mestecky J. The mucosal-immune system in HIV infection and prospects for mucosae immunity to AIDS. AIDS Res Rev 1992, 2:289–312.
38. Forrest B D. The need for consideration of mucosal immunity in vaccine approaches to AIDS. Vaccine Res 1992, 1:137.
39. Padian N D, Shiboski S C, and Jewell N P. Female to male transmission of human immunodeficiency virus. J Amer Med Assoc 1991, 266:1664–1667.

40. Forrest B D. Women, HIV, and mucosal immunity. Lancet 1991, 337:835–836.
41. Miller C J, McGhee J R, and Gardner M B. Mucosal immunity, HIV transmission and AIDS. Lab Invest 1992, 68:129–145.
42. Mestesky J, Kutteh W H, and Jackson S. Mucosal immunity in the female genital tract: relevance to vaccination efforts against the Human Immunodeficiency Virus. AIDS Res Human Retroviruses 1994, 10:511–520.
43. Miller C J, Alexander N J, Sutjipto S, Lackner A A, Hendrickx A G, Lowenstine L J, Jennings M, and Marx P A. Genital musocal transmission of simian immunodeficiency virus: animal model for heterosexual transmission of human immunodeficiency virus, J Virol 1989, 63:4277–4284.
44. Lehner T, Bergmeier L A, Panagiotidi C, Tao L, Brookes R, Klavinskis L S, Walker P, Walker J, Ward R G, and Hussain L: Induction of mucosal and systemic immunity to a recombinant simian immunodeficiency viral protein. Sicence 1992,. 258:1365–1369.
45. Lehner T, Brookes R, Panagiotid C, Tao L., Klavinskis L S, Walker J, Walker P. Ward R, Hussain L, Gearing A J H, Adams S E, and Bergmeier L A. T- and B-cell functions and epitope expression in nonhuman primates immunized with simian immunodeficiency virus antigen by. the rectal route. Proc Natl Acad Sci USA.1993, 90:8638–8642.
46. Marx P A, Compans R W, Gettie A, Staas J K, Gilley R M, Mulligan M J, Yamschikov G V, Chen D, and Eldridge J H. Protection against vaginal SIV transmissiom with microencapsulated vaccine. Science 1993, 260:1323–1327.
47. Mestecky J, and McGhee J R. Immunoglobulin A (IgA): molecular and cellular interactions involved in IgA biosynthesis and immune response. Adv Immunol 1987, 40:153–245.
48. Melnick J L. Enteroviruses: Polioviruses, Coxsackiviruses, Echoviruses, and newer Enteroviruses. In, Virology. Bernard N. Fields and David M. Knipe, eds in chief. Raven Press, New York, N.Y., 1990, 549–605.
49. Mestecky J, Lue C, and Russell M W. Selective transport of IgA: cellular and molecular aspects. Gastroenterol Clin North Amer. 1991, 20:441–471.
50. Mestecky J. The common mucosal immune system and current strategies for induction of immune responses in external secretions. J Clin Immunol 1987, 7:265–276.
51. Papsidero, L D, Sheu, M, and Ruscetti, F W. Human immunodeficiency virus type 1-neutralizing monoclonal antibodies which react with p17 core protein: characterization and epitope mapping. 3J Virol 1989, 63:267–272.
52. Myers G., A. B. Rabson, J. A. Berzofsky, T. F., Smith, and F. Wong-Staal. Human Retroviruses and AIDS. Los Alamos National Laboratory, Los Alamos, N M 1990.
53. Ho, D D, Kaplan, J C, Rackauskas, I E, and Gurney, M E. Second conserved domain of gp120 is important for HIV infectivity and antibody neutralization. Science 1988, 239:1021–1023.
54. Ho D D, Sarngadharan M G, Hirsch M S, Schooley R T, Rota T R, Kennedy R C, Chanh T C, Sato V L. Human immunodeficiency virus neutralizing antibodies recognize several conserved domains on the envelope glycoproteins. J Virol 1987, 61:2024–2028.
55. Rusche J R, Javaherian K, McDanal C, Petro J. Lynn D L, Grimaila R, Langlois A, Gallo R C, Arthur L O, Fischinger P J, Bolognesi D P, Putney S D, and Matthews, T J. Antibodies that inhibit fusion of human immunodeficiency virus-infected cells bind a 24-amino acid sequence of the viral envelope, gp120. Proc Natl Acad Sci USA 1988, 85:3198–3202.
56. Palker T J, Matthews T J, Langlois A, Tanner M E, Martin M E, Scearce R M, Kim J E, Berzofsky J A, Bolognesi D P, Haynes B F . Polyvalent human immunodeficiency virus synthetic immunogen comprised of envelope gp120 T helper. cell sites and B cell neutralization epitopes. J Immunol 1989, 142:3612–3619.
57. Palker T J, Clark M E, Langlois A J, Matthews T J, Weinhold K J, Randall R R, Bolognesi D P, Haynes B F. Type-specific neutralization of the human immunodeficiency virus with antibodies to env-encoded synthetic peptides. Proc Natl Acad Sci USA 1988, 85:1932–1936.
58. Kenealy, W R, Matthews, T J, Ganfield, M-C, Langlois, A J, Waselefsky, D M, and Petteway, S R, Jr. Antibodies from human immunodeficiency virus-infected individuals bind to a short amino acid sequence that elicits neutralizing antibodies in animals. AIDS Res Human Retrovirus 1,989, 5:173–181.
59. Javaherian K, Langlois A J, McDanal C, Ross K L, Eckler L I, Jellis C L, Profy A T, Rusche J R, Bolognesi D P, Putney S D. Principal neutralizing domain of the human immunodeficiency virus type 1 envelope protein. Proc Natl Acad Sci USA 1989, 86:6768–6772.
60. Chanh T C, Dreesman G R, Kanda P, Linette G P, Sparrow J T, Ho D D, Kennedy R C. Induction of anti-HIV neutralizing antibodies by synthetic peptides. EMBO J 1986, 5:3065–3071.
61. Schrier, R D, Gnann, J W, Jr., Langlois, A J, Shriver, K, Nelson, J A, and Oldstone, M B. B- and T- lymphocyte responses to an immunodominant epitoe of human immunodeficiency virus. J Virol 1988, 62:2531–2536.
62. Evans D J, McKeating J, Meredith J M, Burke K L, Katrak K, John A, Ferguson M, Minor P D, Weiss R A, Almond J W. An engineered poliovirus chimaera elicits broadly reactive HIV-1 neutralizing antibodies. Nature 1989, 339:385–388.
63. Sun N C, Ho D D, Sun C R, Liou R S, Gordon W, Fung M S, Li X L, Ting R C, Lee T H, Chang N T. Generation and characterization of monoclonal antibodies to the putative CD4-binding domain of human immunodeficiency virus type 1. gp120. J Virol 1989, 63:3579–3585.
64. Goudsmit J, Debouck C, Meloen R H, Smit L, Bakker M, Asher D M, Wolff A V, Gibbs C J Jr., Gajdusek D C. Human immunodeficiency virus type 1 neutralization epitope with conserved architecture elicits early type-specific antibodies in experimentally infected chimpanzees. Proc Natl Acad Sci USA 1988, 85:4478–4482.
65. Meloen, R H, Liskamp, R M, and Goudsmit, J. Specificity and function of, the individual amino acids of an important determinant of human immunodeficiency virus type 1 that induces neutralizing activity. J Gen Virol 1989, 70:1505–1512.
66. Marthas M L, Sutjipto S, Higgins J, Lohman B, Torten J, Luciw P A, Marx P A, Pedersen N C. Immunization with a live, attenuated simian immunodeficiency virus (SIV) prevents early disease but not infection in rhesus macaques challenged with pathogenic SIV. J Virol 1990, 64:3694–3700.
67. Goudsmit, J, Krone, W J, and Wolfs, T F W. Genomic divergence within the coding sequence for the principal neutralization epitope of HIV-1. Quatrième Colloque des Cent Gardes, L' Institut Pasteur, Marnes-La-Coquette, France, 1989, 55–60.
68. Putney, S, Larosa, G, and Mathews, T. The principal neutralizing determinant of HIV-1. Quatrième Colloquedes Cent Gardes, L'Institut Pasteur, Marnes-la-Coquette, France, 1989, 189–193.

69. Bolognesi, D P. General Features of the V3 neutralization loop of HIV. Quatrième Colloque des Cent Gardes, L'Institut Pasteur, Marnes-La-Coquette, France, 1989, 181–188.
70. Carrow, E, Vujcic, L, Hendry, R, Galvao, F, Halsey, N, Boulos, R, and Quinnau, G. Geographically diverse antibody responses to the variable region 3 (V3:) neutralizing epitope of the HIV-1 envelope. VI Intl Conf on AIDS, San Francisco, Calif., 1990, #S.A. 281.
71. Putney, S, Larosa, G, Lewis, J, Profy, A, Weinhold, K, Matthews, T, Boswell, N, Dreesman, G, Holley, H, Karpus, M, Emini, E, and Bolognesia, D. The HIV-1 principal neutralizing determinant contains conserved sequences and structural elements. VI-Intl Conf on AIDS, San Francisco, Calif., 1990, #F.A.211.
72. Katzenstein D A, Vujcic L K, Latif A, Boulos R, Halsey N A, Quinn T C, Rastogi S C, Quinnan G V Jr. Human immunodeficiency virus neutralizing antibodies in sera from North Americans and Africans. J Acq Imm Def Syn 1990, 3:810–816.
73. McKeating, J A, Gow, J, Goudsmit, J, Pearl, L H, Mulder, C, and Weiss, R A. Characterization of HIV-1 neutralization escape mutants. AIDS 1989, 3:777–784.
74. Kuiken, C L, DeJong, J-J, Tersmette, M, Smit, L, Nara, P L, and Goudsmit, J. Changes in a neutralization domain of sequential isolates in experimental and natural HIV infection. VI Intl Conf on AIDS, San Francisco, Calif., 1990, #S.A.278.
75. Wolfs, T F W, Goudsmit, J, DeJong, J-J, Kuiken, C L, Van den Berg, H and Krone, W J A. Individual selection for genetic variants of the V3 major neutralizing domain. VI Intl Conf on AIDS, San Francisco, Calif., 1990, #S.A.279.
76. Vujcic, L, Carrow, E, Seamon, K, and Quinnan, G. Periodic changes in neutralization epitopes of HIV-1-involve variable region 3. VI Intl Conf on AIDS, San Francisco, Calif., 1990, #S.A.277.
77. Robert-Guroff, M, Reitz, M S, Jr., Robey, W G, and Gallo, R C. In vitro generation of an HTLV-III variant by neutralizing antibody. J Immunol 1986, 137:3306–3309.
78. Reitz, M S, Jr., Wilson, C, Naugle, C, Gallo,. R C, and Robert-Guroff, M. Generation of a neutralization-resistant variant of HIV-1 is due to selection for a point mutation in the envelope gene. Cell 1988, 54:57–63.
79. Albert, J, Abrahamsson, B, Nagy, K, Aurelius E, Gaines H, Nystrom G, Fenyo E M. Rapid development of isolate-specific neutralizing antibodies after primary HIV-1 infection and consequent emergence of virus variants which resist neutralization by autologous sera. AIDS 1990, 4:107–112.
80. Wilson C, Reitz M S Jr., Aldrich K, Klasse P J, Blomberg J, Gallo R C, Robert-Guroff M. The site of an immune-selected point mutation in the transmembrane protein of human immunodeficiency virus type1 does not constitute the neutralization epitope. J Virol 1990, 64:3240–3248.
81. Nara P L, Smit L, Dunlop N, Hatch W, Merges M, Waters D, Kelliher J, Gallo R C, Fischinger P J, Goudsmit J. Emergence of viruses resistant to neutralization by V3-specific antibodies in experimental human immunodeficiency virus type 1 IIIB infection of chimpanzees. J Virol 1990, 64:3779–3791.
82. Weiss, R A, Clapham, P R, Cheingsong-Popov, R. Daigleish, A G, Carne, C A, Weller, N D , and Tedder, R S. Neutralization of human T-lymphotropic virus type III by sera of AIDS and AIDS-risk patients. Nature 1985, 316:69–72.
83. Weiss, R A, Clapham, P R, Weber, J N, Dalgleish, A G, Lasky, L A, and Berman, P W. Variable and conserved neutralization antigens of human immunodeficiency virus. Nature 1986, 324:572–575.
84. Berkower, I, Smith, G E, Giri, C, and Murphy, D. Human immunodeficiency virus 1: predominance of a group-specific neutralizing epitope that persists despite genetic variation. J Exp Med 1989, 170:1681–1695.
85. Nara, P L, Garrity, R R, and Goudsmit, J. Neutralization of HIV-1: a paradox of humoral proportions. FASEB J. 1991, 5:2437–2455.
86. Ho, D D, Li, X L, Daar, E S, Mondgil, T, Sun, N C, Holton, D, and Robinson, J E. A neutralizing human monoclonal antibody (HMab) identifies an epitope within the putative CD4-binding domain (CD4-BD) of HIV-1 gp120. VI Intl Conf on AIDS, San Francisco, Calif., 1990, #Th.A.76.
87. Weiss R A, Clapham P R, McClure M O, McKeating J A, McKnight A, Dalgleish A G, Sattentau Q J, Weber J N. Human immunodeficiency viruses: neutralization and receptors. J Acq Imm Def Syn 1988, 1:536–541.
88. Larkin M, Childs R A, Matthews T J, Thiel S, Mizuochi T, Lawson A M, Savill J S, Haslett C, Diaz R, Feizi T. Oligosaccharide-mediated interactions of the envelope glycoprotein gp120 of HIV-1 that are independent of CD4 recognition. AIDS 1989, 3:793–798.
89. Qureshi, N M, Coy, D H, Garry, R F, and Henderson, L A. Characterization of a putative cellular receptor for HIV-1 transmembrane glycoprotein using synthetic peptides. AIDS 1990, 4:553–558.
90. Broliden, P. A., Ljunggren, K., Hinkula, J., Norrby, E., Akerblom, L., and Wahren, B. A monoclonal antibody to human immunodeficiency virus type 1 which mediates cellular cytotoxicity and neutralization. J Virol 1990, 64:936–940.
91. Dowbenko D, Nakamura G, Fennie C, Shimasaki C, Riddle L, Harris R, Gregory T, Lasky L. Epitope mapping of the human immunodeficiency virus type 1 gp120 with monoclonal antibodies. J Virol 1988, 62:4703–4711.
92. Desgranges C, Boyer V, Souche S, Sprecher S. Burney A, Gallo R C, Bernard J, Reveil B, Zagury D. Monoclonal antibodies to HIV in a non-infected, immunised volunteer. Lancet 1988, 935–936.
93. Thali, M, Olshevsky, U, Furman, C, Gabuzda, D, Posmer, M, and Sodroski, J. Characterization of a discontinuous human immunodeficiency virus type 1 gp120 epitope recognized by a broadly reactive neutralizing humanmonoclonal antibody. J. Virol. 1991, 65:6188–6193.
94. Hansen J E, Clausen H, Nielsen C, Teglbjaerg L S, Hansen L L, Nielsen C M, Dabelsteen E, Mathiesen L, Hakomori S I, Nielsen J O. Inhibition of human immunodeficiency virus (HIV) infection in vitro by anti carbohydrate monoclonal antibodies: peripheral glycosylation of HIV envelope glycoprotein gp120 may be a target for virus neutralization. J Virol 1990, 64:2833–2840.
95. Müller, WEG, Schröder, H C, Reuter, P, Maidhof, A, Uhlenbruck, G, and Winkler, I. Polyclonal antibodies to mannan from yeast also recognize the carbohydrate structure of gp120 of the AIDS virus: an approach to raise neutralizing antibodies to HIV-1 infection in vitro. AIDS 1990, 4:159–162.
96. Gruters R A, Neefjes J J, Tersmette M, de Goede R E, Tulp A, Huisman H G, Miedema F, Ploegh H L. Interference with HIV-induced syncytium formation and viral infectivity by inhibitors of trimming glucosidase. Nature 1987, 330:74–77.
97. Walker B D, Kowalski M, Goh W C, Kozarsky K, Krieger M, Rosen C, Rohrschneider L, Haseltine W A, Sodroski J. Inhibition of human immunodeficiency virus syncytium formation and virus replication by castanospermine. Proc Natl,Acad Sci USA 1987, 84:8120–8124.

98. Sunkara, P S, Bowlin, T L, Liu, P S, and Sjoerdsma, A. Antiretroviral activity of castanospermine and deoxynojirimycin, specific inhibitors of glycoprotein processing. Biochem Biophys Res Commun 1987, 148:206–210.

99. Tyms AS, Berrie E M, Ryder T A, Nash R J, Hegarty M P, Taylor D L, Mobberley M A, Davis J M, Bell E A, Jeffries D J. Castanospermine and other plant alkaloid inhibitors of glucosidase activity block the growth of HIV. Lancet 1987, ii:1025–1026.

100. Montefiori, D C, Robinson, W E, Jr., and Mitchell, W M. Role of protein N-glycosylation in pathogenesis of human immunodeficiency virus type 1. Proc Natl Acad Sci USA 1988, 85:9248–9252.

101. Fenouillet, E, Gluckman, J C, and Bahraoui, E. Role of N-linked glycans of envelope glycoproteins in infectivity of human immunodeficiency virus type 1. J Virol 1990, 64:284–2848.

102. Matthews, T J, Weinhold, K J Lyerly, H K, Langlois, A J, Wigzell, H, and Bolognesi, D. Interaction between the human T-cell lymphotropic virus type IIIB envelope. glycoprotein gp120 and the surface antigen CD4: role of carbohydrate in binding and cell fusion. Proc Natl Acad Sci USA 1987, 84:5424–5428.

103. Lifson, J, Coutre, S, Huang, E, and Engleman, E. Role of envelope glycoprotein carbohydrate in human immunodeficiency virus (HIV) infectivity and virus-induced cell fusion. J Exp Med 1986, 164:2101–2106.

104. Robinson, W E, Jr., Montefiori, D C, and Mitchell, W M. Evidence that mannosyl residues are involved in human immunodeficiency virus type 1 (HIV-1) pathogenesis. AIDS Res Human Retrovirus 1987, 3:265–282.

105. Ezekowitz, R A B, Kuhlman, M, Groopman, J E, and Byrn, R A. A human serum mannose-binding protein inhibits in vitro infection by the human immunodeficiency virus. J Exp Med 1989, 169:185–196.

106. Müller, W E G, Renneisen, K, Kreuter, M H, Schröder, H C, and Winkler, I. The D-mannose-specific lectin from Gerardia savaglia blocks binding of human immunodeficiency virus type 1 to H9 cells and human lymphocytes in vitro. J Acq Imm Def Syn 1988, 1:453–458.

107. Haigwood N L, Shuster J R., Moore G K, Lee H, Skiles P V, Higgins K W, Barr P J, George-Nascimento C, Steimer K S. Importance of hypervariable regions of HIV-1 gp120 in the generation of virus neutralizing antibodies. AIDS Res Human Retrovirus 1990, 6:855–869.

108. Matsushita S, Robert-Guroff M, Rusche J, Koito A, Hattori T, Hoshino H, Javaherian K, Takatsuki 7K, Putney S. Characterization of a human immunodeficiency virus neutralizing monoclonal antibody and mapping of the neutralizing epitope. J Virol 1988, 62:2107–2114.

109. Skinner M A, Ting R, Langlois A J, Weinhold K J, Lyerly H K, Javaherian K, Matthews T J. Characteristics of a neutralizing monoclonal antibody to the HIV envelope glycoprotein. AIDS Res Human Retrovirus 1988, 4:187–197.

110. Robinson W E Jr, Montefiori D C, and Mitchell W M. A human immunodeficiency virus type 1 (HIV-1) infection-enhancing factor in seropositive sera. Biochem Biophys Res Commun 1987, 149:693–699.

111. Robinson W E Jr, Montefiori D C, and Mitchell W M. Antibody-dependent enhancement of Human Immunodeficiency Virus Type 1 infection. Lancet 1988, i:790–794.

112. Porterfield J S. Antibody-dependent enhancement of viral infectivity. Adv Virus Res 1986, 31:335–7355.

113. Halstead S B. Pathogenesis of dengue: challenges to molecular biology. Science 1988, 239;476–481.

114. Halstead S B, and O'Rourke E J. Antibody-enhanced dengue virus infection in primate leukocytes. Nature 1977, 265:739–741.

115. Kliks S C, Nisalak A, Brandt W E, Wahl L, and Burke D S. Antibody-dependent enhancement of dengue virus growth in human monocytes as a risk factor for dengue hemorrhagic fever. Am J Trop Med Hyg 1989, 40:444–451.

116. Hawkes R A. Enhancement of the infectivity of arboviruses by specific antisera produced in domestic fowls. Aust J Exp Biol Med Sci 1964, 42:465–482.

117. Cecilia D, Gadkari D A, Kedarnath N, and Ghosh S N. Epitope mapping of Japanese encephalitis virus envelope protein using monoclonal antibodies against an Indian strain. J Gen Virol 1988, 69:–2741–2747.

118. Peiris J S M, and Porterfield J S. Antibody-mediated enhancement of Flavivirus replication in macrophage-like cell lines. Nature 1979, 282:509–511.

119. Cardosa M J, Porterfield J S, and Gordon S. Complement receptor mediates enhanced flavivirus replication in macrophages. J Exp Med 1983, 158:258–263.

120. Schlesinger J J, and Brandriss M W. Growth of 17D yellow fever virus in a macrophage-like cell line, U937: role of Fc and viral receptors in antibody-mediated. infection. J Immunol 1981,127:659–665.

121. Barrett A D T, and Gould, E A. Antibody-mediated early death in vivo after infection with yellow fever virus. J Gen Virol 1986, 67:2539–2542.

122. Phillpotts R J, Stephenson J R, and Porterfield J S. Antibody-mediated enhancement of tick-borne encephalitis virus infectivity. J Gen Virol 1985, 66:1831–1837.

123. Peiris J S M, and Porterfield J S. Antibody-dependent plaque enhancement: its antigenic specificity in relation to Togaviridae. J Gen Virol 1982, 58:291–296.

124. King A A, Sands J J, and Porterfield J S. Antibody-mediated enhancement of rabies virus infection in a mouse macrophage cell line (P388D1). J Gen Virol 1984, 65:1091–1093.

125. Chanas A C, Gould E A, Clegg J C S, and Varma M G R. Monoclonal antibodies to Sindbis virus glycoprotein E1 can neutralize, enhance infectivity, and independently inhibit haemagglutination or haemolysis. J Gen Virol 1.982, 58:37–46.

126. Vennema H, deGroot R J, Harbour D A, Dalderup M, Gruffydd-Jones T, Horzinek M C, and Spaan W J M. Early death after feline infectious peritonitis virus challenge due to recombinant vaccinia virus immunization. J Virol 1990, 64:1407–1409.

127. Chin J. Magoffin R L, Shearer L A, Schieble J H, and Lennette E H. Field evaluation of a respiratory syncytial virus vaccine and a trivalent parainfluenza virus vaccine in a pediatric population. Am J Epidemiol 1969, 89:449–463.

128. Fulginiti V A, Eller J d, Sieber O F, Joyner J W, Minamitani M, and Meiklejohn G. Respiratory virus immunization I. A field trial of two inactivated respiratory virus vaccines; an aqeuous trivalent parainfluenza virus vaccine and an alum-precipitated respiratory syncytial virus vaccine. Am J Epidemiol 1969, 89:435–448.

129. Kim H W, Canchola J G, Brandt C D, Pyles G, Chanock R M, Jensen K, and Parrott R H. Respiratory syncytial virus disease in infants despite prior administration of antigenic inactivated vaccine. Am J Epidemiol 1969, 89:422–434.

130. Kapikian A Z, Mitchell R H, Chanock R M, Shvedoff R A, and Stewart, C E. An epidemiologic study of altered clinical reactivity to respiratory syncytial (RS) virus infection in children previously vaccinated with an inactivated RS virus vaccine. Am J Epidemiol 1969, 89:405–421.

131. Prince G A, Jenson A B, Hemming V G, Murphy B R, Walsh E E, Horswood R L, and Chanock R M. Enhancement of respiratory syncytial virus pulmonary pathology in cotton rats by prior intramuscular inoculation of formalin-inactivated virus. J Virol 1986, 57:721–728.

132. Fulginiti V A, Eller J J, Downie A W, and Kempe C H. Altered reactivity to measles virus: atypical measles in children previously immunized with inactivated measles virus vaccines. J Am Med Assoc 1967, 202:1075–1080.

133. Rauh L W, and Schmidt R. Measles immunization with killed virus vaccine: serum antibody titers and experience with exposure to measles epidemic. Amer J Dis Child 1965, 109:232–237.

134. McGuire T C, Adams D S, Johnson G C, Klevjer-Anderson P, Barbee D D, and Gorham J R. Acute arthritis in caprine arthritis-encephalitis virus challenge exposure of vaccinated or persistently infected goats. Am J Vet Res 1986, 47:537–540.

135. Knowles D Jr, Cheevers W, McGuire T, Stem T, and Gorham J. Severity of arthritis is predicted by antibody response to gp135 in chronic infection with caprine arthritis-encephalitis virus. J Virol 1990, 64:2396–2398.

136. Robinson W E Jr, Montefiori D C, and Mitchell W M. A human immunodeficiency virus type 1 (HIV-1) infection-enhancing factor in seropositive sera. Biochem Biophys Res Commun 1987, 149:693–699.

137. Robinson W E Jr, Montefiori D C, and Mitchell W M. Antibody-dependent enhancement of human immunodeficiency virus type 1 infection. Lancet 1988, i:790–794.

138. Robinson W E Jr, Montefiori D C, Gillespie D H, and Mitchell W M. Complement-mediated, antibody-dependent enhancement of HIV-1 infection in vitro is characterized by increased protein and RNA synthesis and infectious virus release. J Acq Imm Def Syn 1989, 2:33–42.

139. Robinson W E Jr, Montefiori C D, and Mitchell W M. Complement-mediated antibody-dependent enchancement of HIV-1 infection requires CD4 and complement receptors. Virology 1990, 175:600–604.

140. Homsy J, Tateno M, and Levy J A. Antibody-dependent enhancement of HIV infection. Lancet 1988, i:1285–1286.

141. June R A, Schade S Z, Bankowski M J, Kuhns M, McNamara A, Lint T F, Landay A L, and Spear G T. Complement and antibody mediate enhancement of HIV infection by increasing virus binding and provirus formation. AIDS 1991, 5:269–274.

142. June R A, Landay A L, Stefanik K, Lint T F, and Spear G T. Phenotypic analysis of complement receptor 2+ T lymphocytes: reduced expression on CD4+cells in HIV-infected persons. Immunology 1992, 75:59–65.

143. Robinson W E Jr, Kawamura T, Gorny M K, Montefiori D C, Mitchell W M, Luke D, Matsumoto Y, Sugano T, Masuho Y, Hersh E, and Zolla-Pazner S. Human monoclonal antibodies to the human immunodeficiency virus type 1 (HIV-1) transmembrane glycoprotein gp41 enhance HIV-1 infection in vitro. Proc Natl Acad Sci USA 1990, 87:3185–3189.

144. Robinson W E Jr, Kawamura T, Lake D, Masuho Y, Mitchell W M, and Hersh E M. Antibodies to the primary immunodominant domain of human immunodeficiency virus type 1 (HIV-1) glycoprotein 41 enhance HIV-1 infection in vitro. J Virol 1990, 64:5301–5305.

145. Robinson W E Jr, Gorny M K, Xu J-Y, Mitchell W M, and Zolla Pazner S A. Two immunodominant domains of gp41 bind antibodies which enhance HIV-1 infection in vitro. J Virol 1991, 65:4169–4176.

146. Klasse P J, Pipkorn R, and Blomberg J. Presence of antibodies to a putatively immunosuppressive part of human immunodeficiency virus (HIV) envelope glycoprotein gp41 is strongly associated with health among HIV-positive subjects. Proc Natl Acad Sci USA 1988, 85:5225–5229.

147. Gnann J W Jr, Nelson J A, and Oldstone M B A. Fine mapping of an immunodominant domain in the transmembrane glycoprotein of human immunodeficiency virus. J Virbl 1987, 61:2639–2641.

148. Chiodi F A, Gegerfeldt J, Albert E M, Fenyö E M, Gaines H, von Sydow M, Biberfeld G, Parks E, and Norrby E. Site directed ELISA with synthetic peptides representing the HIV transmembrane glycoprotein. J Med Virol 1987, 23:1–9.

149. Moore J P, Jameson B A, Weiss R A, and Sattentau Q J. The HIV-cell fusion reaction. In: *Viral Fusion Mechanisms*, Bentz, J., ed., CRC Press, Boca Raton, Fla., 1993, 233–289

150. Mitchell W M, Torres J, Johnson P R, Hirsch V, Yilma T, Gardner M B, and Robinson W E Jr. Antibodies to the putative SIV infection-enhancing domain diminish beneficial effects of an SIV gp160 vaccine in rhesus macaques. AIDS 1995, in press.

151. Mills K H, Page M, Chan W L, Kitchin P, Stott E J, Taffs F, Jones W, Rose J, Ling C, and Silvera P. Protection against SIV infection in macaques by immunization with inactivated virus from the BK28 molecular clone but not with BK28-derived recombinant env and gag proteins. J Med Primatol 1992, 21:50–58.

152. Giavedoni L D, Planelles V, Haigwood N L, Ahmad S, Kluge J D, Marthas M L, Gardner M B, Luciw P A, and Yilma T D. Immune response of rhesus macaques to recombinant simian immunodeficiency virus gp130 does not protect from challenge infection. J Virol 1993, 67:577–583.

153. Berman P W, Gregory T J, Riddle L, Nakamura G R, Champe M A, Porter J P, Wurm F M, Hershberg R D, Cobb E K, and Eichberg J W. Protection of chimpanzees from infection after vaccination with recombinant glycoprotein gp120 but not gp160. Nature 1990, 345:622–625.

154. Hu S L, Fultz P N, McClure H M, Eichberg J W, Thomas E K, Zarling J, Singhal M C, Kosowski S G, Swenson R B, Anderson D C, and Todaro G. Effect of immunization with a Vaccinia-HIV env recombinant on HIV infection of chimpanzees. Nature 1987, 328:721–721.

155. Berman P W, Groopman J E, Gregory T, Clapham P R, Weiss R A, Ferriani R, Riddle L, Shimasaki C, Lucas C, Lasky L A, and Eichberg J W. Human immunodeficiency virus type 1 challenge of chimpanzees immunized with recombinant envelope glycoprotein gp120. Proc Natl Acad Sci USA 1988, 85:5200–5204.

156. Wang S Z, Rushlow K E, Issel C J, Cook R F, Cook S J, Raabe M L, Chong Y-H, Costa L, and Montelaro R C. Enhancement of EIAV replication and disease by immunization with a baculovirus-expressed recombinant envelope surface glycoprotein. Virology 1994, 199:2347–251.

157. Gardner M B, Rosenthal A, Jennings M, Yee J, Antipa L, and MacKenzie M. Passive immunization of macaques against SIV infection. J Med, Primatol 1994, in press.

158. Robinson J W E, Torres J V, and Gardner M. Antibodies to amino acid 603–622 of simian immunodeficiency virus (SIV) transmembrane glycoprotein apparently enhance SIV infection in rhesus macaques. First National Conference on Human Retroviruses and Related Infections. Washington, D.C., December 1993, abstract 79.

159. Putkonen P, Thortensson R, Ghavamzadeh L, Albert J, Hild K, Biberfeld G, and Norrby E. Prevention of HIV-2 and SIVsm infection by passive immunization in cynomolgus monkeys. Nature 1991, 352:436–438.

160. Hohdatsu, T., Pu R, Torres B A, Trujillo S, Gardner M B, and Yamamoto J C. Passive antibody protection of cats against feline immunodeficiency virus infection. J Virol 1993, 67:2344–2348.

161. Hosie M J, Osborne R, Reid G, Neil J C, and Jarrett 0. Enhancement after feline immunodeficiency virus vaccination. Vet Immunol Immunopathol 1992, 35:191–197.

162. Kent K A, Kitchin P, Mills K H G, Page M, Taffs F, Corcoran T, Silvera P, Flanagan B, Powell C, Rose J, Ling C, Aubertin A M, and Stott E J. Passive immunization of cynomolgus macaques with immune sera or a pool of neutralizing monoclonal antibodies failed to protect against challenge with $SIV_{mac251}$. AIDS Res Hum Retroviruses 1994, 10:189–194.

163. Daar E S, Moudgil T, Meyer R D, and Ho D D. Transient high levels of viremia in patients with primary human immunodeficiency virus type 1 infection. N Engl J Med 1991, 324:961–964.

164. Clark S J, Saag M S, Decker W D, Campbell-Hill S, Roberson J L, Veldkamp P J, Kappes J C, Hahn B, and Shaw G M. High titers of cytopathic virus in plasma of patients with symptomatic primary HIV-1 infection. N Engl J Med 1991, 324:954–960.

165. Boucher C A B, Lange J M A, Miedema F F, Weverling G J, Koot M, Mulder J W, Goudsmit J, Kellam P, Larder B A, and Tersmette M. HIV-1 biological phenotype and the development of zidovudine resistance in relation to disease progression in asymptomatic individuals during treatment. AIDS 1992, 6:1259–1264.

166. Taylor J G M, Schwartz K, and Detels R. The time from infection with human immunodeficiency virus (HIV) to the onset of AIDS. J Infect Dis 1986, 154:694–697.

167. Roos M T L, Lange J M A, de Goede R E Y, Coutinho R A, Schellekens P T A, Miedema F, and Tersmette M. Viral. phenotype and immune response in primary human immunodeficiency virus type I infection. J Infect Dis 1992, 165:427–432.

168. Bozzette S A, McCutchan J A, Spector S A, Wright B, and Richman D D. A cross-sectional comparison of persons with syncytium-and non-syncytium-inducing human immunodeficiency virus. J Infect Dis 1993, 168:1374–1379.

169. Koot M, Keet I P M, Vos A H V, Goede R E Y, Roos MThL, Coutinho R A, Miedema F, Schellekens PThA, and Tersmette M. Prognostic value of HIV-1 syncytium-inducing phenotype for rate of CD4+cell depletion and progression to AIDS. Ann. Int Med 1993, 118:681–688.

170. Nielsen C, Pedersen C, Lundgren J D, and Gerstoft J. Biological properties of HIV isolates in primary HIV infection: consequences for the subsequent course of infection. AIDS 1993, 7:1035–1040.

171. Zhu T, Mo H, Wang N, Nam D S, Cao Y, Koup R A, and Ho D D. Genotypic and phenotypic characterization of HIV-1 in patients with primary infection. Science.¹993, 261:1179–1181.

172. Gabriel J L, and Mitchell W M. Proposed atomic; structure of atruncated human immunodeficiency virus glycoprotein gp120 derived by molecular modeling: target CD4 recognition and docking mechanism. Proc Natl Sci USA 1993, 90:4186–4190.

173. LaRosa G J, Davide J P, Weinhold K, Waterbury J A, Profy A T, Lewis J A, Langlois A J, Dreesman G R, Boswell R N, Shadduck P, Holley L H, Karplus M, Bolognesi D P, Matthews T J, Emini E A, and Putney S D. Conserved sequence and structural elements in the HIV-1 principal neutralization determinant. Science 1990, 249:932–935.

174. Leonard C K, Spellman M W, Riddle L, Harris R J, Thomas J N, and Gregory T J. Assignment of intrachain disulfide bonds and characterization of potential glycosylation sites of the type 1 recombinant human immunodefidiency virus envelope glycoprotein (gp120 ) expressed in Chinese hamster ovary cells. J Biol Chem 1990, 265:10373–10382.

175. Ebenbichler C, Westervelt P, Carrillo A, Henkel T, Johnson D, and Ratner L. Structure-function relationships of the HIV-1 envelope V3 loop tropism determinant: evidence for two distinct conformations. AIDS 1993, 7:639–646.

176. Gu R, Westervelt P, and Ratner L. Role of HIV-1 envelope V3 loop cleavage in cell tropism. Aids Res Hum Retrovir 1993, 9:1007–1015.

177. Tindall B, and Cooper D A. Primary, HIV infection: host responses and intervention strategies. AIDS 1991, 5:1–14.

178. Robinson W E Jr, and Mitchell W M. Neutralization and enhancement of in vitro and in vivo HIV and SIV infection. AIDS 1990, 4:S151–S162.

179. Gabriel J L, and Mitchell W M. GP120 docking interactions and inhibition design based on an atomic structure derived by molecular modeling using the Dreiding II Force Field. Proceedings of the Distance-based approaches to protein structure determination II Symposium, 1994, in press.

180. Freed E, Myers J D, and Risser R. Mutational analysis of the cleavage sequence of the human immunodeficiency virus type 1 envelope glycoprotein precursor gp60. J Virol 1989, 63:4670–4675.

181. Pinter A, Honnen W J, Tilley S A, Bona C, Zaghouani H, Gorney M K, and Zolla-Pazner S. Oligomeric structure of gp41, the transmembrane protein of human immunodeficiency virus type 1. J Virol 1989, 63:2674–2679.

182. Chada S, De JeSus C E, Townsend K, Lee W T L, Laube L, Jolly D J, Change S M W, and Warner J F. Cross-reactive lysis of human targets infected with prototypic and clinical Human Immunodeficiency Virus Type (HIV-1) strains by murine auto-HIV-1 IIIB env-specific cytotoxic T lymphocytes. J Virol 1993, 67:3409–3417.

183. Aslandis C, and DeJong P U. Ligation-independent. cloning of PCR products (LIC-PCR). Nuc Acid Res 1990, 18:6069–6074.

184. Haun R A, Servanti I M, and Moss J. Rapid, reliable ligation-independent cloning of PCR products using modified plasma vectors. BioTechniques 1992, 13:515–518.

185. Montefiori D C, Robinson W E, Schuffman S S, and Mitchell W M. Evaluation of antiviral drugs and neutralizing antibodies against human immunodeficiency virus by a rapid and sensitive microtiter infection assay. J Clin Microbiol 1988, 26:231–235.

186. Dalgleish, A G, Chanh, T C, Kennedy, R C, Kanda, P, Clapham, P R, and Weiss, R A. Neutralization of diverse HIV-1 strains by monoclonal antibodies raised against a gp41 synthetic peptide. Virology 1988, 165:209–215.

187. Mitchell W M, and Rosenbloom T. Induction of mucosal and humoral anti-HIV responses with HIV env-DNA. Keystone Symposium on Mucosal Immunity: New Strategies for Protection Against Viral and Bacterial Pathogens. Jan 1995, Keystone, Colo.
188. Sambrook et al., *Molecular Cloning*: A Laboratory Manual, 2nd Ed., Cold Spring Harbor Laboratory, Cold Spring Harbor, N.Y., 1989
189. Fundamental Virology, 2nd Ed. Bernard N. Fields and David M. Knipe, Chief Eds., Raven Press:New York, 1990 190. Martin, E. W. (ed.) *Remington's Pharmaceutical Sciences*, latest edition Mack Publishing Co., Easton, Pa.
191. *Mechanisms of Microbial Disease*, 2nd Ed., Moselio Schaechter, Gerald Medoff and Barry I. Eisenstein, Eds., Williams & Wilkins, Baltimore, 1993.

What is claimed is:

1. A method of inducing a mucosal immune response to antigen in a mammal, comprising administering to the mucosa of said mammal antigen-encoding DNA, operably linked to a promoter for expression of said antigen and complexed to a transfection-facilitating lipospermine or lipospermidine, in an amount effective to induce a mucosal immune response to expressed antigen.

2. The method of claim 1, wherein the mucosal administration is nasal.

3. The method of claim 1, wherein the mucosal administration is oral.

4. The method of claim 1, wherein the mucosal administration is rectal.

5. The method of claim 1, wherein the mucosal administration is vaginal.

6. The method of claim 1, wherein the lipospermine is dioctadecylamidboglycylspermine.

7. The method of claim 1, wherein the DNA encodes an envelope antigen or envelope-associated antigen.

* * * * *